United States Patent
Blakey et al.

(10) Patent No.: US 10,004,633 B2
(45) Date of Patent: Jun. 26, 2018

(54) LIQUID DROPLET DISPENSER

(71) Applicant: Glaxo Group Limited, Brentford, Middlesex (GB)

(72) Inventors: David Blakey, Ware (GB); Gary Thomas Crosby, Ware (GB)

(73) Assignee: Glaxo Group Limited, Brentford, Middlesex (GB)

( * ) Notice: Subject to any disclaimer, the term of this patent is extended or adjusted under 35 U.S.C. 154(b) by 529 days.

(21) Appl. No.: 14/425,640

(22) PCT Filed: Sep. 4, 2013

(86) PCT No.: PCT/EP2013/068316
§ 371 (c)(1),
(2) Date: Mar. 4, 2015

(87) PCT Pub. No.: WO2014/037420
PCT Pub. Date: Mar. 13, 2014

(65) Prior Publication Data
US 2015/0209178 A1    Jul. 30, 2015

Related U.S. Application Data

(60) Provisional application No. 61/697,849, filed on Sep. 7, 2012.

(51) Int. Cl.
*A61F 9/00* (2006.01)
*B05B 11/00* (2006.01)

(52) U.S. Cl.
CPC .......... *A61F 9/0008* (2013.01); *B05B 11/309* (2013.01)

(58) Field of Classification Search
CPC .............................. A61F 9/0008; B05B 11/309
See application file for complete search history.

(56) References Cited

U.S. PATENT DOCUMENTS

| | | | | |
|---|---|---|---|---|
| 3,174,655 | A | * | 3/1965 | Hurschman ................ F16N 3/04 222/215 |
| 5,810,778 | A | * | 9/1998 | Hjertman ............ A61M 5/1454 604/143 |
| 2005/0023300 | A1 | * | 2/2005 | Schultz ................. A61F 9/0008 222/383.1 |
| 2009/0236445 | A1 | | 9/2009 | Lintern et al. |

FOREIGN PATENT DOCUMENTS

| | | | | |
|---|---|---|---|---|
| IT | WO 2011121406 | A1 * | 10/2011 | ......... B65D 83/0005 |
| WO | 91/06338 | A1 | 5/1991 | |
| WO | 2011/121406 | A1 | 10/2011 | |

* cited by examiner

*Primary Examiner* — Tatyana Zalukaeva
*Assistant Examiner* — Jessica Arble
(74) *Attorney, Agent, or Firm* — Robert J. Smith

(57) ABSTRACT

A dispenser for the delivery of a droplet of a liquid comprises a housing which defines an outlet orifice, a tip seal, biased against the housing to seal the outlet orifice, and a dosing pump for pumping a liquid to the outlet nozzle. The dispenser further comprises an actuation pump configured to provide a hydraulic opening force to the tip seal for opening of the outlet orifice. Preferably the actuation pump is configured to operate at a higher pressure than the dosing pump.

20 Claims, 38 Drawing Sheets

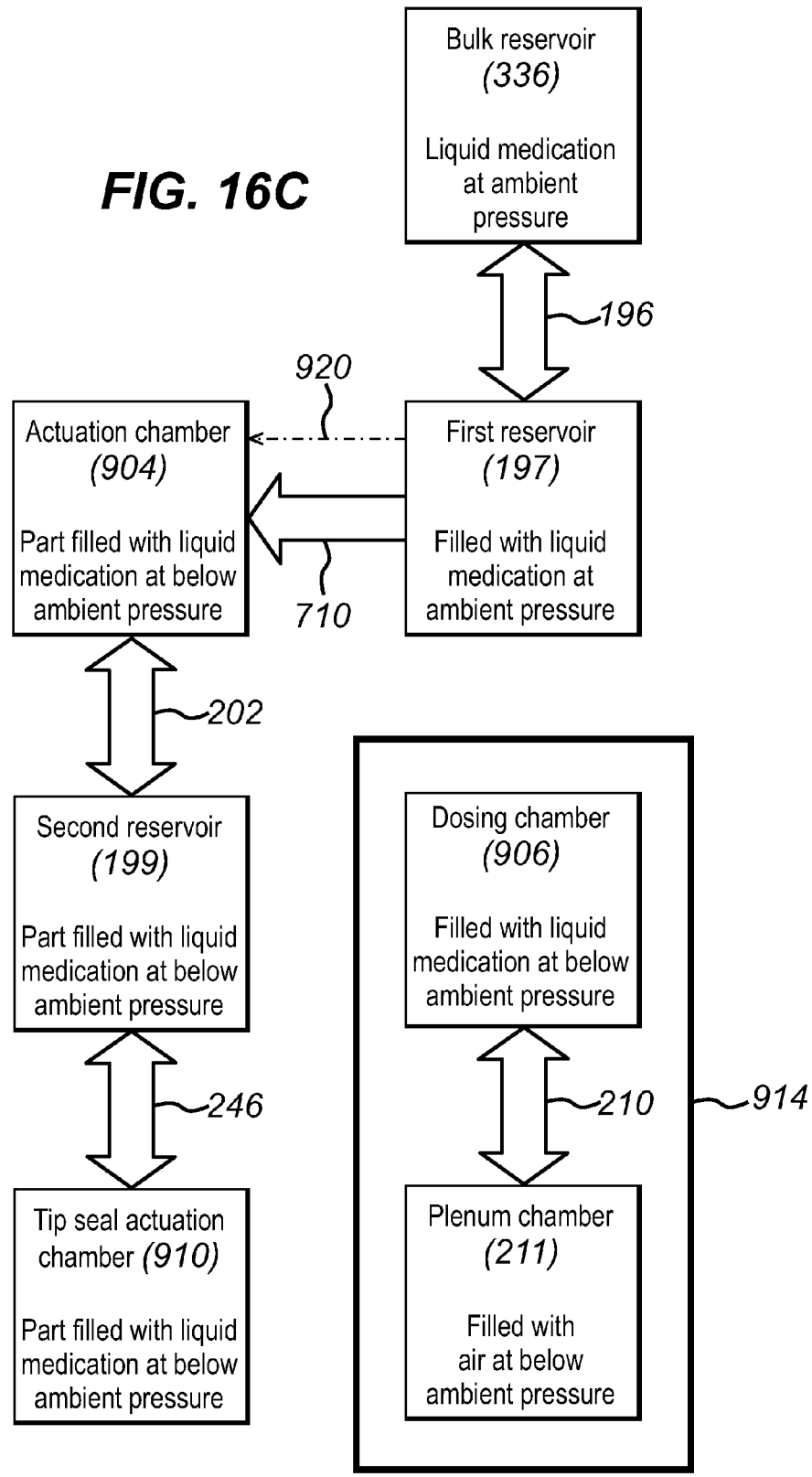

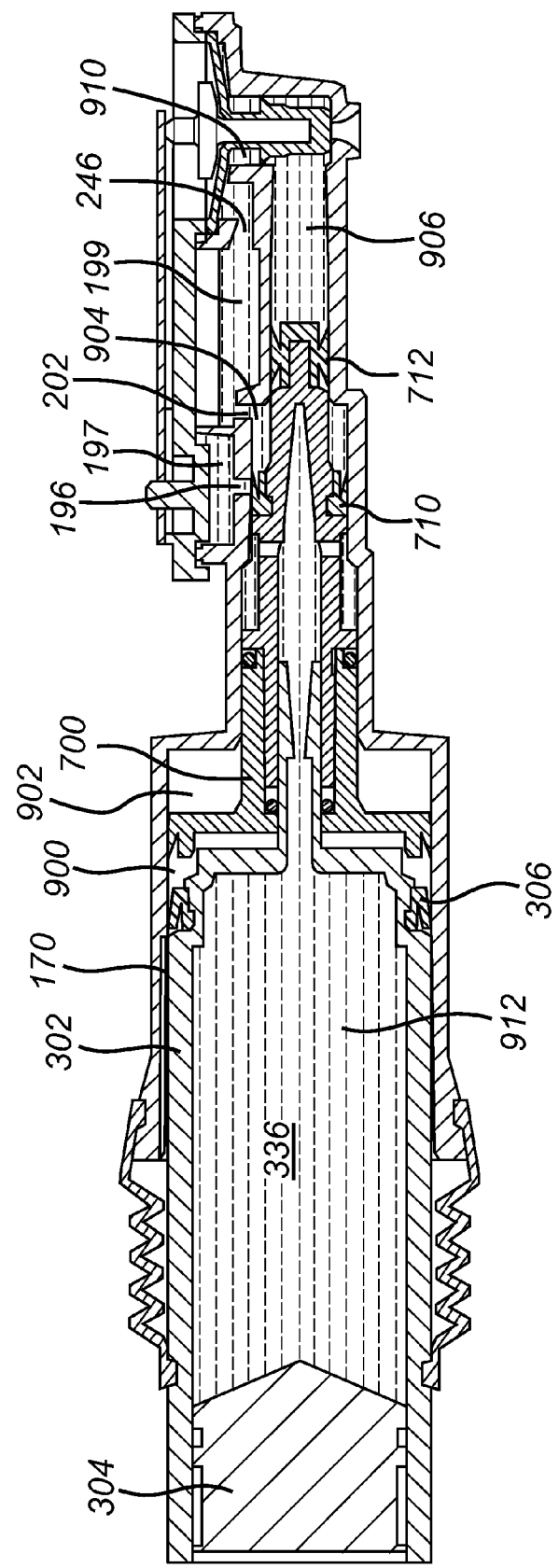

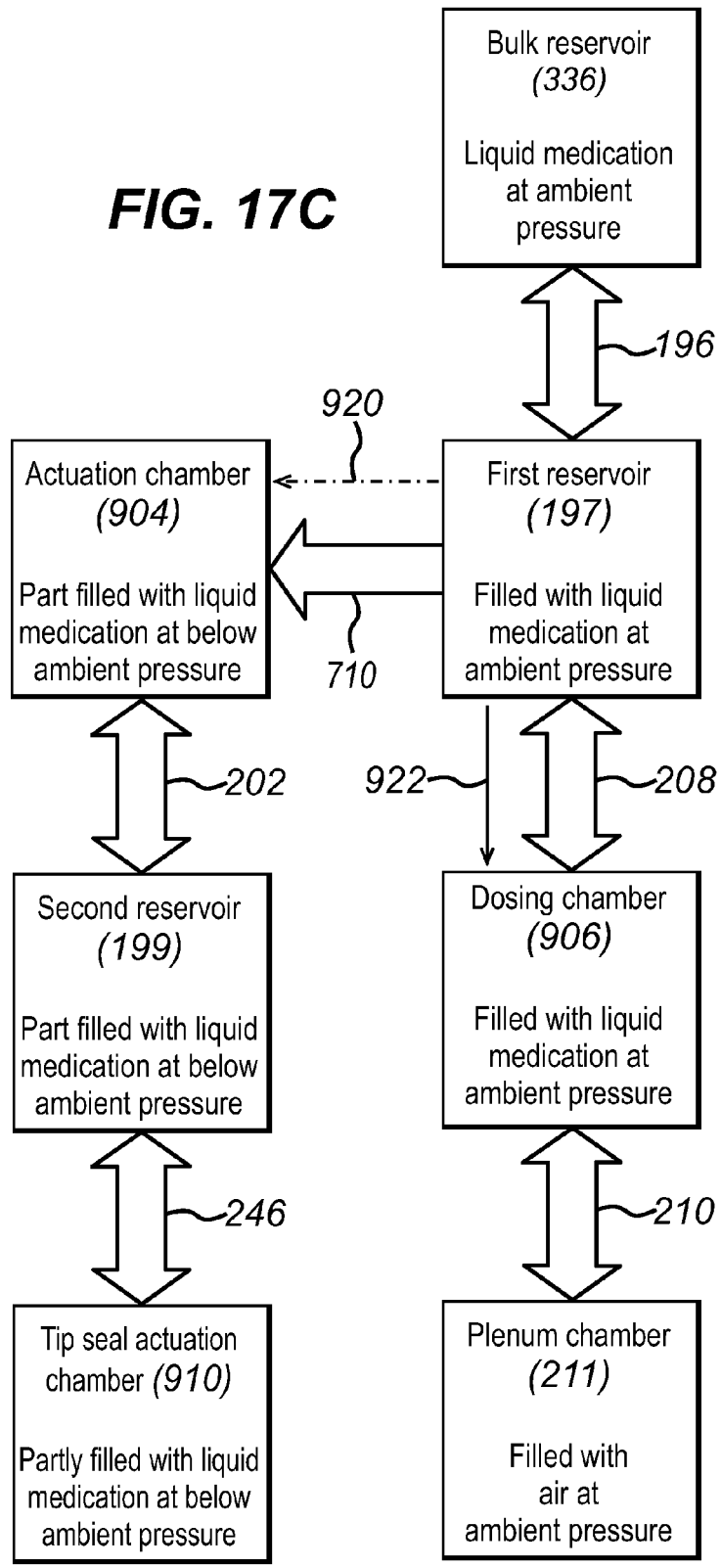

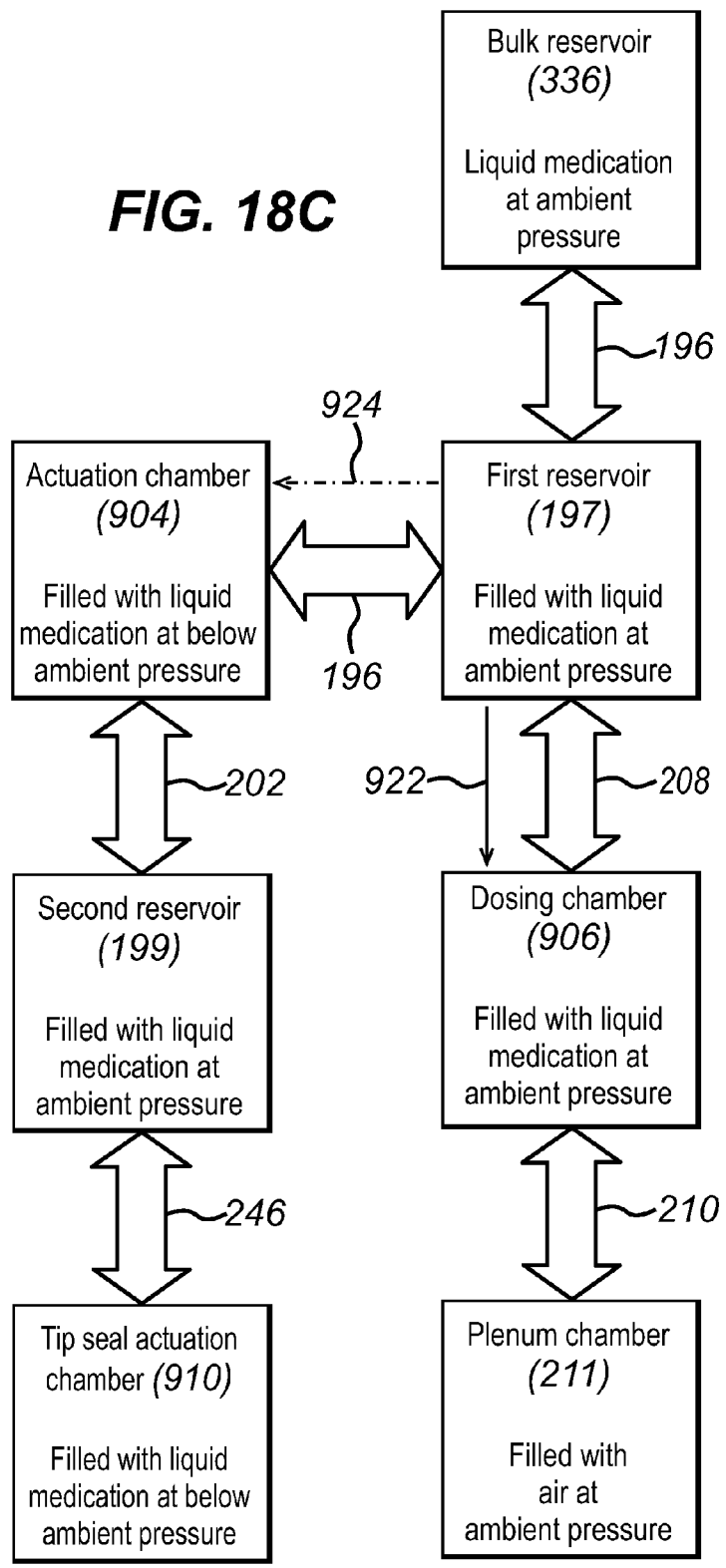

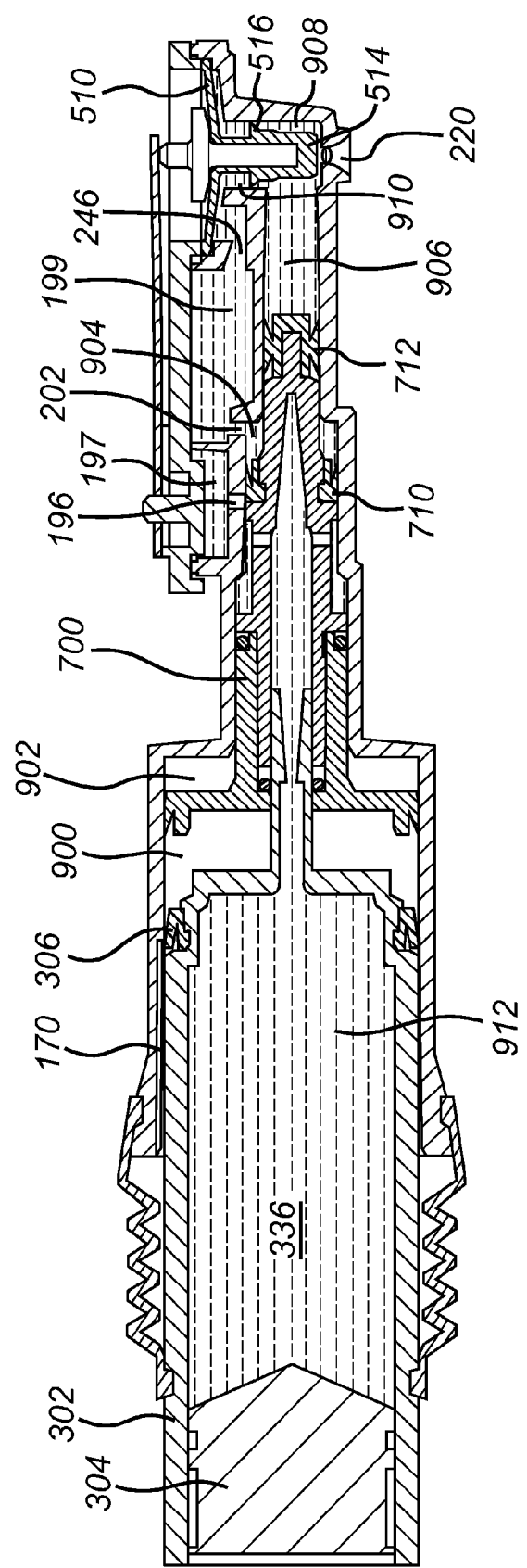

LIQUID DROPLET DISPENSER

CROSS-REFERENCE TO RELATED APPLICATIONS

This application is filed pursuant to 35 U.S.C. § 371 as a United States National Phase Application of International Application No. PCT/EP2013/068316 filed 4 Sep. 2013 which claims priority from U.S. Provisional Application No. 61/697,849 filed 7 Sep. 2012.

The present invention concerns a device for delivering a liquid in droplet form. The present invention particularly concerns a device suitable for the delivery of a metered dose of a liquid medication, in single droplet form, to the eye of a patient. The device is particularly suited for the storage, and delivery of a preservative free liquid medication.

The present invention also concerns a method of delivering a metered dose, in droplet form, of a liquid. The present invention particularly concerns a method of delivering a droplet of liquid medication to the eye of a patient.

The present invention also concerns an actuator suitable for, but not limited to, use with a device for delivering a metered dose of a liquid medication in droplet form.

SUMMARY OF THE INVENTION

According to a first aspect of the present invention, there is provided a dispenser for the delivery of a droplet of a liquid, comprising a housing which defines an outlet orifice, a tip seal, biased against the housing to seal the outlet orifice, and a dosing pump for pumping a liquid to the outlet nozzle, wherein the dispenser further comprises an actuation pump configured to provide a hydraulic opening force to the tip seal for opening of the outlet orifice.

Suitably, the actuation pump is configured to operate at a higher pressure than the dosing pump.

Preferably, the dosing pump is pressurised to between 0.002 bar and 0.095 bar during operation.

Preferably, the actuation pump is pressurised to about 1.77 bar during operation.

Preferably the droplet is delivered with low hydraulic energy. More preferably this energy is between 0.03252 mJ/s and 0.120 mJ/s.

Preferably, the actuation pump provides the hydraulic opening force to the tip seal via a tip actuation chamber.

Preferably the tip actuation chamber is separated from the dosing chamber by the interaction of the tip seal and the dispenser housing.

Preferably the tip seal is provided with a lip seal which engages the dispenser housing to separate the dosing pump from the tip actuation chamber.

Preferably the lip seal is shaped to enable some leakage from dosing pump to the actuation chamber, but not from the actuation chamber to the dosing pump.

Suitably, operation of the dispenser causes the dosing pump to be primed before the actuation pump is primed.

Suitably, the dosing pump and actuation pump are provided by a common component.

Suitably, the common component is a piston.

Suitably, the piston is a stepped piston.

Suitably the device is configured such that in use, delivery of the droplet comprises a first phase during which the dosing pump contracts at a first speed, and a second phase during which the delivery pump contracts at a second, higher speed.

Suitably, the dosing pump is partly defined by the tip seal such that operation of the tip seal causes the different effective speeds in contraction of the dosing pump during the first and second phase of opening.

Suitably, the actuation pump and dosing pump use a common liquid.

Suitably, the common liquid is supplied from a common reservoir.

Preferably the common liquid is a medication. More preferably, the medication is a preservative-free medication.

Suitably, the actuation pump is in part defined between a first seal and a second seal, and wherein the actuation pump is configured such that motion of at least one seal controls liquid flow into the actuation pump.

Suitably, the actuation pump is in part defined between a first seal and a second seal, and the actuation pump is configured such that motion of at least one seal controls liquid flow out of the actuation pump.

Preferably, one or both of these seals is a lip seal.

Preferably, one or both of these seals is mounted to a piston for sliding motion within a bore provided to the dispenser housing.

Preferably, the at least one seal controls liquid flow out of the actuation pump in cooperation with a conduit provided to the housing of the device.

Suitably, the actuation pump is in part defined between a first seal and a second seal, and the actuation pump is configured such that motion of the first seal controls the liquid flow into the actuation pump, and the second seal controls liquid flow out of the actuation pump.

Preferably, one or both of these seals is a lip seal. More preferably an annular lip seal.

Preferably, one or both of these seals is mounted to a piston for sliding motion within a bore provided to the dispenser housing.

Preferably, the first seal controls liquid flow into the actuation pump in cooperation with a conduit provided to the housing of the device.

Preferably, the second seal controls liquid flow out of the actuation pump on cooperation with a conduit provided to the housing of the device.

Suitably, the dosing pump is in part defined between a first seal and a second seal, and at least one seal controls liquid flow into, and out of, the dosing pump.

Preferably, one or both of these seals is a lip seal. More preferably the seal is an annular lip seal.

Preferably, one or both of these seals is mounted to a piston for sliding motion within a bore provided to the dispenser housing.

Preferably, the first seal controls liquid flow into, and out of, the dosing pump in cooperation with a conduit provided to the housing of the device.

Suitably, the first seal controls liquid flow into and out of the dosing pump, and the second seal controls liquid flow out of the dosing pump.

Suitably, the second seal comprises the tip seal.

Suitably, the actuation pump and dosing pump share a common seal.

Preferably, the common seal is a lip seal. More preferably the seal is an annular lip seal.

Preferably, the seal is mounted to a piston for sliding motion within a bore provided to the dispenser housing.

Preferably, the common seal controls liquid flow out of the actuation pump, and controls liquid flow into, and out of, the dosing pump.

Preferably, the common seal cooperates with a conduit provided to the dispenser housing to control liquid flow out of the actuation pump.

Preferably, the common seal cooperates with a conduit provided to the dispenser housing to control liquid flow into, and out of, the dosing pump.

Preferably the common seal cooperates with a single conduit to control liquid flow out of the actuation pump, and to control liquid flow into, and out of, the dosing pump.

Suitably, the common seal controls the volume of the dispensed droplet in conjunction with the device housing.

Preferably, the common seal controls the volume of the dispensed droplet in conjunction with the common conduit provided to the device housing.

Suitably, the device comprises a gas filled plenum in flow communication with the dosing pump.

Preferably, this gas is an inert gas, such as nitrogen.

According to a further aspect of the present invention, there is provided an actuator for a medication dispenser comprising a movable coupling and a first vacuum chamber, wherein the movable coupling is provided with a driver, operable to move the coupling in a first direction to expand the first vacuum chamber, wherein movement of the driver in the first direction expands the first vacuum chamber from a contracted state, and wherein release of the driver allows the first vacuum chamber to return to the contracted state, moving the coupling in a second direction, independent of the driver.

Preferably, the driver is a drive piston. Preferably the drive piston also provides a reservoir for a liquid.

Preferably the coupling is an intermediate vacuum seal which couples with a piston that forms a liquid dispensing pump and or an actuation pump.

Suitably, the actuator further comprises a housing, and the first vacuum chamber is defined by the housing and by the coupling.

Suitably, the coupling is slidably sealed against the housing.

Suitably, the coupling is slidingly sealed against the housing by a first seal and a second seal, and the first vacuum chamber is defined between the first seal and the second seal, and between the coupling and the housing.

Suitably, the housing defines a bore, and the coupling is slidably received within the bore.

Suitably, the driver is selectively coupled to the dispenser coupling by a second vacuum chamber.

Suitably, the second vacuum chamber is provided with a vacuum release which operates to vent the second vacuum chamber when the first vacuum chamber is expanded to a predetermined size, thereby decoupling the driver from the first vacuum chamber.

Preferably, the vacuum release is configured to control the rate of contraction of the first vacuum upon decoupling of the driver from the first vacuum chamber.

Suitably, the actuator comprises a housing, and the second vacuum chamber is defined by the housing and the coupling and by the driver.

Suitably, the vacuum release comprises at least one vent provided to the actuator.

Preferably the vent comprises a flute.

Suitably, the vent is positioned such that the second vacuum chamber is vented at a predetermined expansion of the first vacuum chamber.

Suitably, the actuator comprises a seal adapted to allow one way flow past the seal, out of the first vacuum chamber.

Preferably the seal is a lip seal.

Preferably the lip seal is formed integral with the coupling.

Suitably the actuator comprises a seal adapted to allow one way flow past the seal, out of the second vacuum chamber.

Preferably the seal is a lip seal.

Preferably the lip seal is formed integral with the coupling.

According to a further aspect of the present invention, there is provided a method of delivering a droplet of medication comprising the steps of;

filling a dosing pump with a medication, and then filling an actuation pump with the medication, then contracting the actuation pump and contracting the dosing pump, such that a tip seal is lifted away from an outlet orifice by the contraction of the actuation pump, and then venting the actuation pump to close the tip seal against the outlet orifice to seal it, wherein contraction of the dosing pump delivers a dose of the medication to the outlet nozzle at a first speed as the tip seal is lifted away from the outlet orifice, and at a second, higher speed as the tip seal is closed against the outlet nozzle.

Suitably, the method comprises the further steps of expanding a first vacuum chamber from a contracted state as the dosing pump is filled, and as the actuation pump is filled, and then allowing the vacuum chamber to contract to the contracted state, wherein the vacuum chamber is coupled to the dosing pump and the actuation pump such that the contraction of the vacuum chamber drives the contraction of the actuation pump and contraction of the dosing pump.

Suitably, the method comprises the further step of bleeding liquid medication from the dosing pump in a first stage of contraction of the dosing pump.

Other aspects and exemplary features of the invention are to be found in the exemplary embodiments which will now be described, by way of example only, with reference to the accompanying Figures of drawings.

BRIEF DESCRIPTION OF FIGURES OF DRAWINGS

Figure 15A:
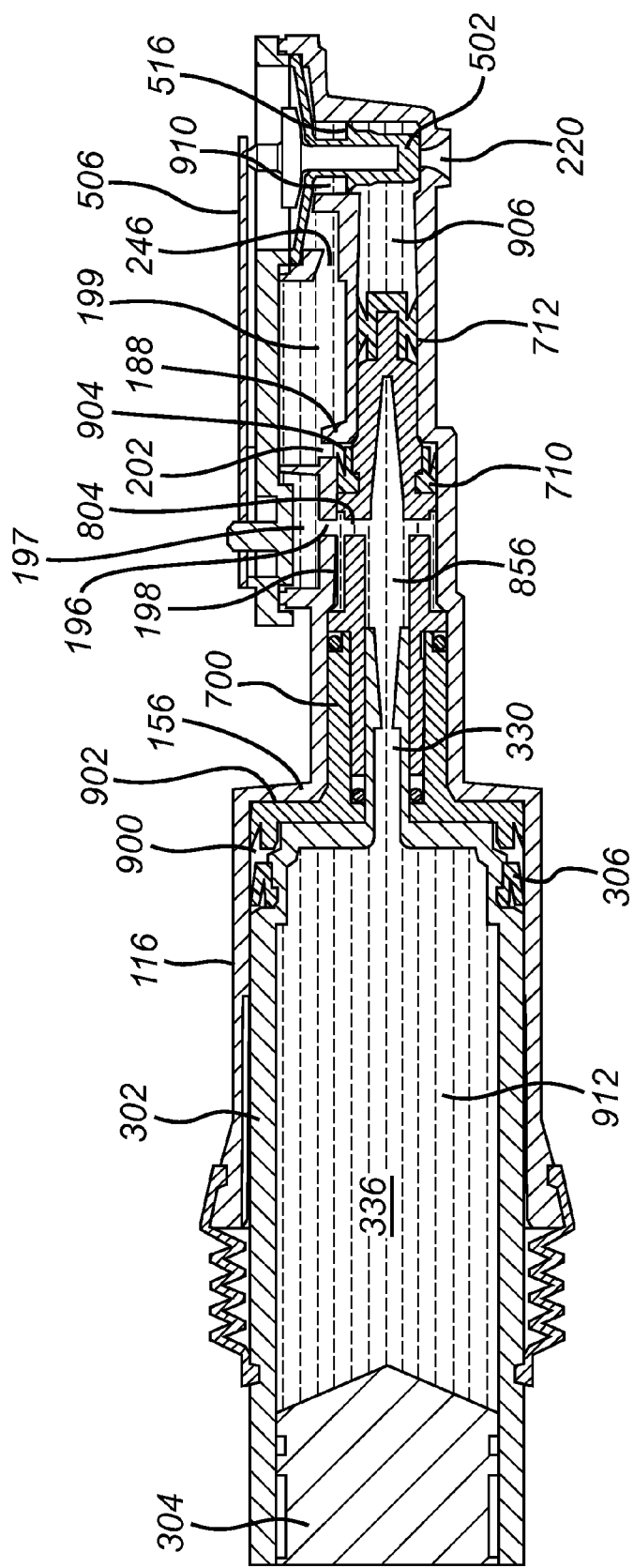
FIG. 15A shows a first section through the device at rest.
Figure 15B:
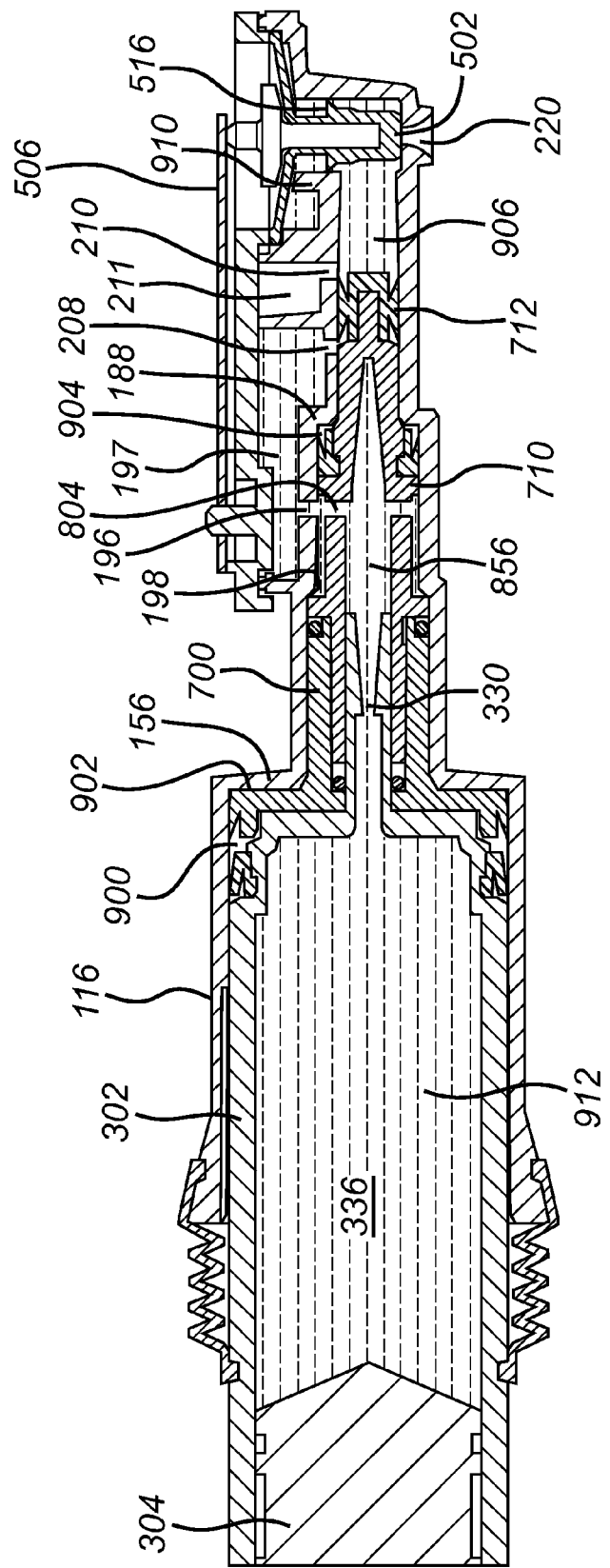
FIG. 15B shows a second section through the device at rest.
Figure 15C:
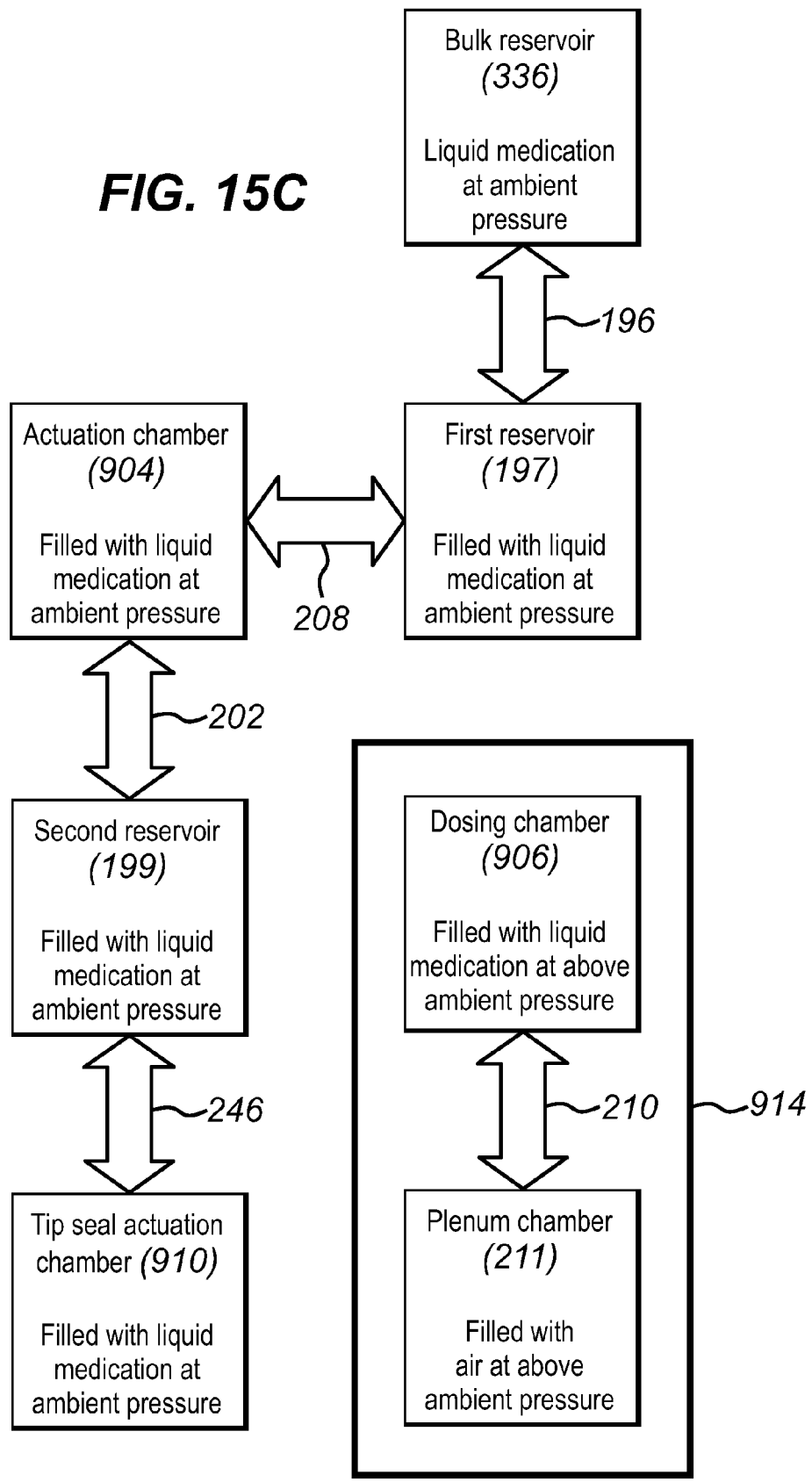

FIG. 15C provides a flow diagram to illustrate flow paths within the device at rest.

Figure 16A:
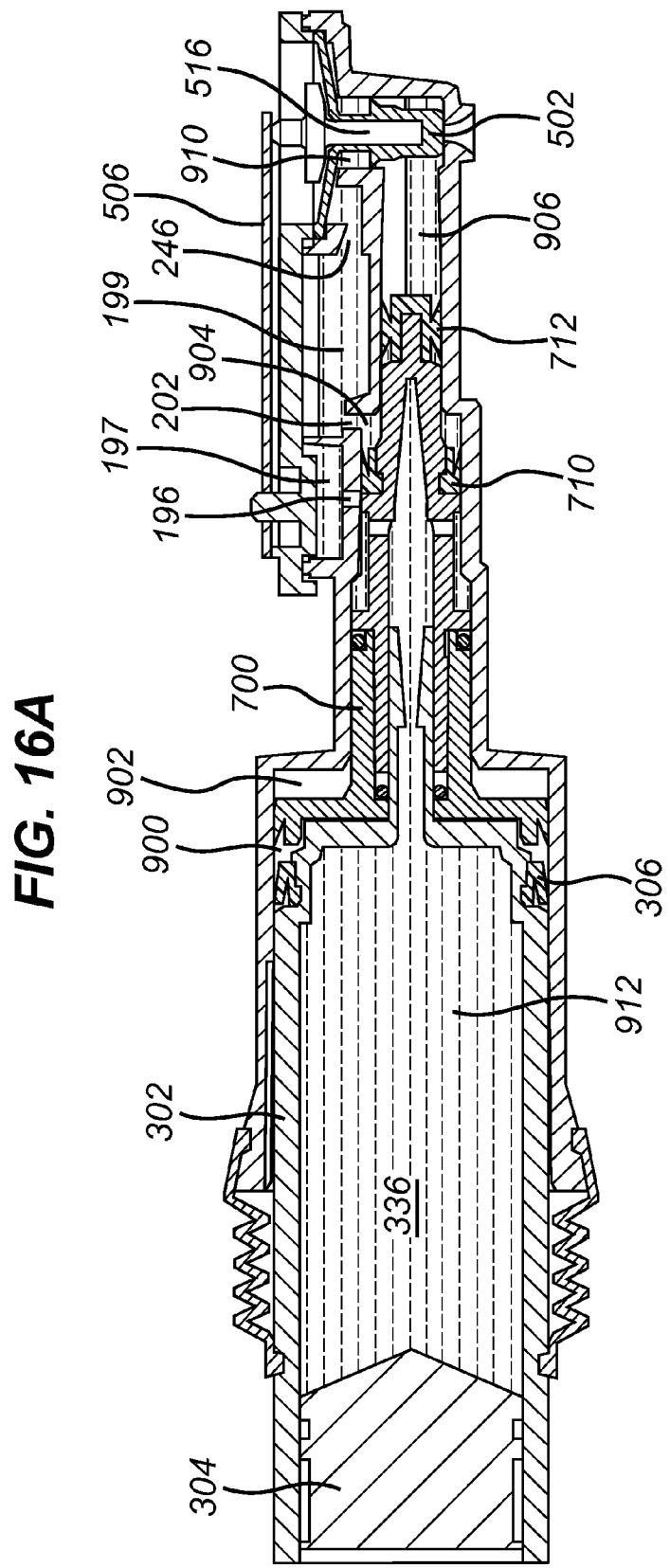
Figure 16B:
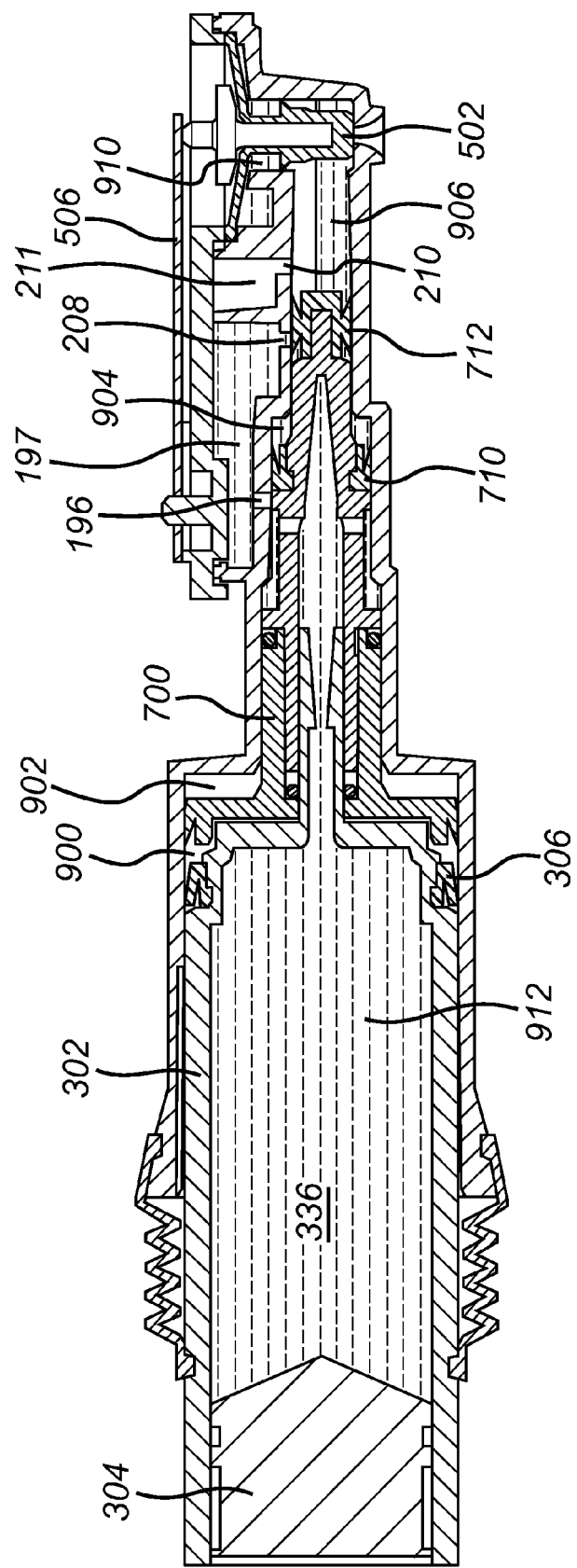

FIGS. 16A, 16B, and 16C show the same views as FIGS. 15A, 15B and 15C in a first stage of actuation of the device, also known as the first priming phase.

Figure 17B:
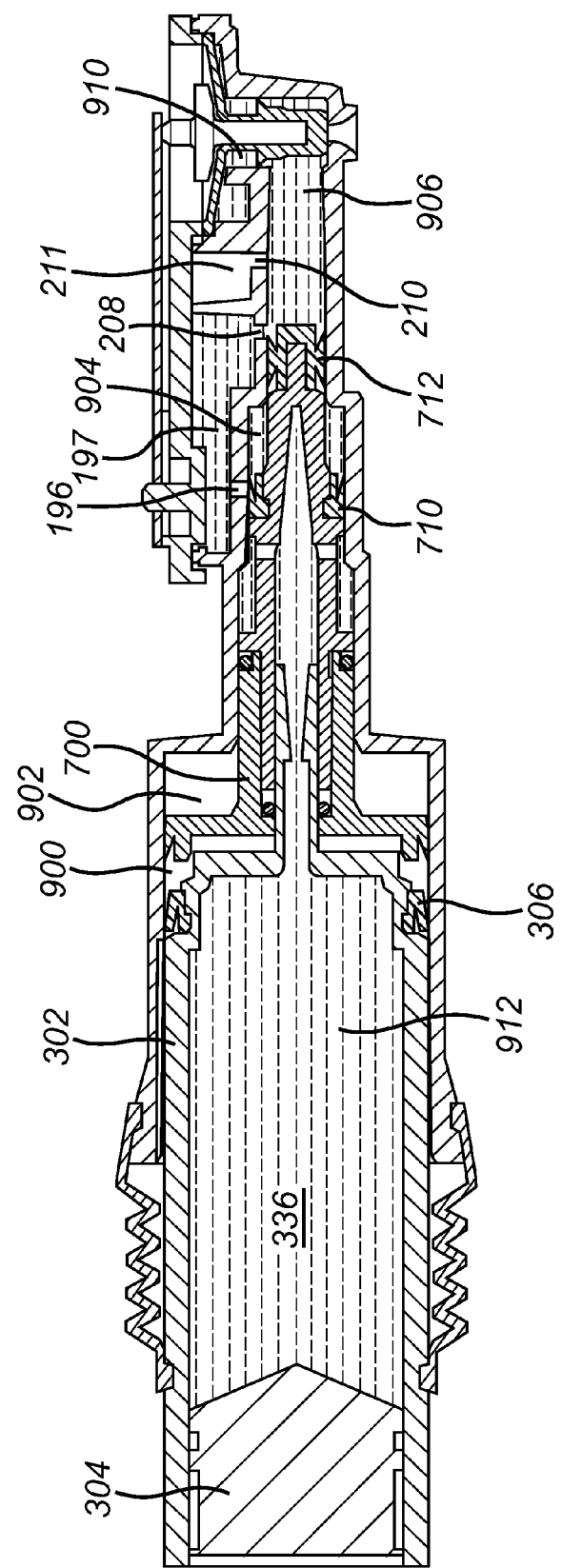

FIGS. 17A, 17B, and 17C show the same views as FIGS. 15A, 15B and 15C in a second stage of actuation of the device, also known as the second priming phase.

Figure 18A:
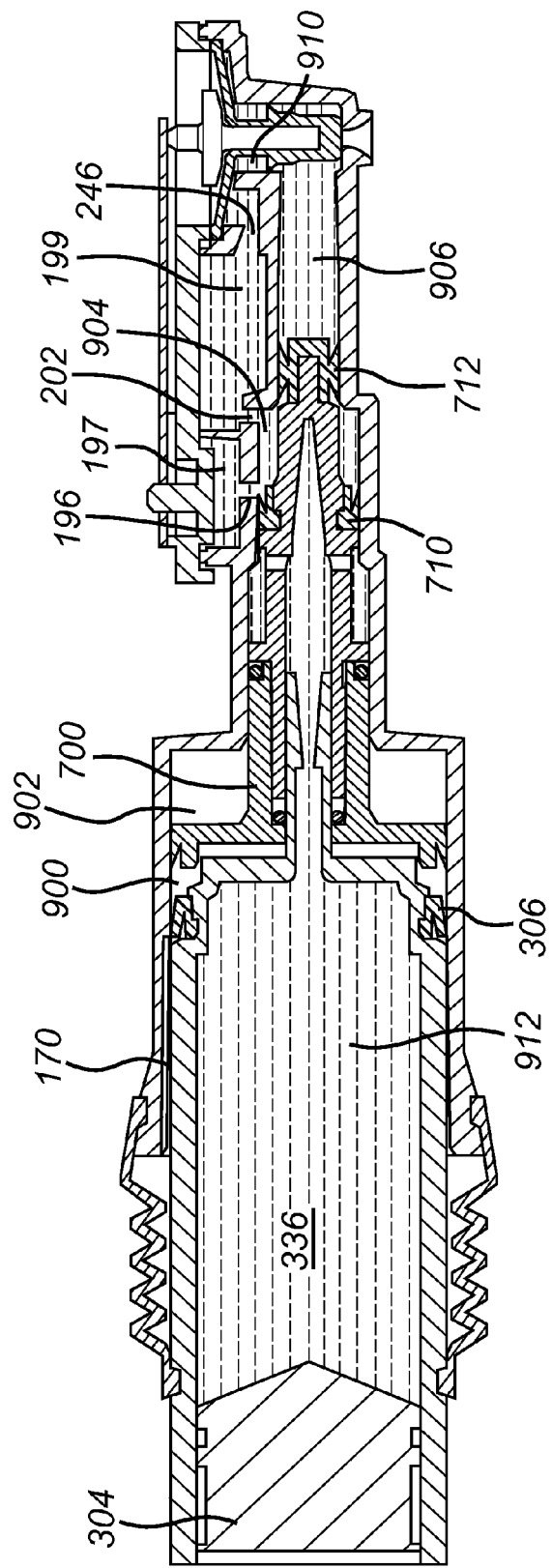
Figure 18B:
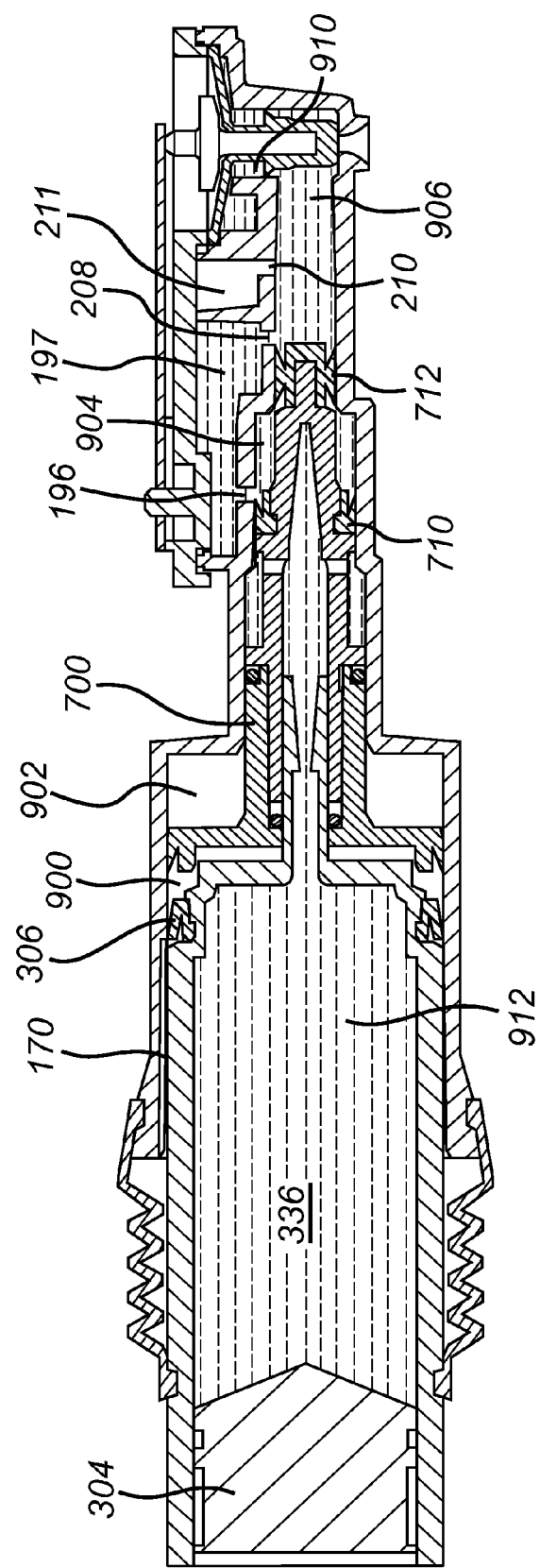

FIGS. 18A, 18B, and 18C show the same views as FIGS. 15A, 15B and 15C in a third stage of actuation of the device, also known as the third priming phase.

Figure 19A:
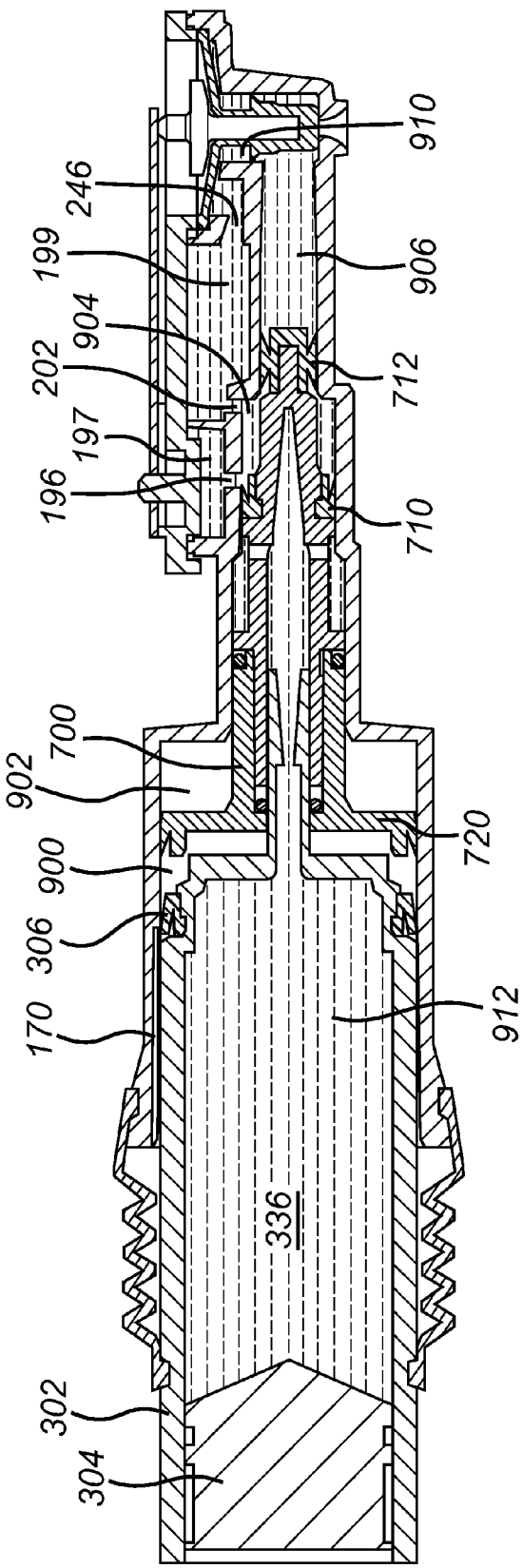
Figure 19B:
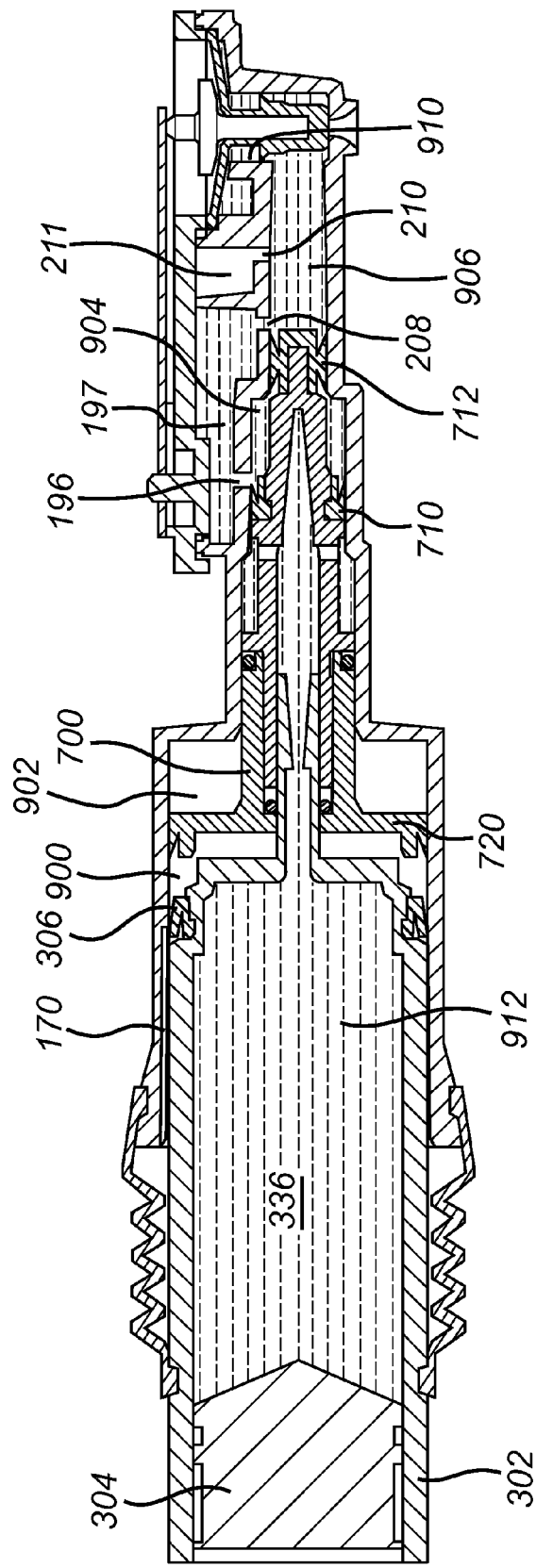
Figure 19C:
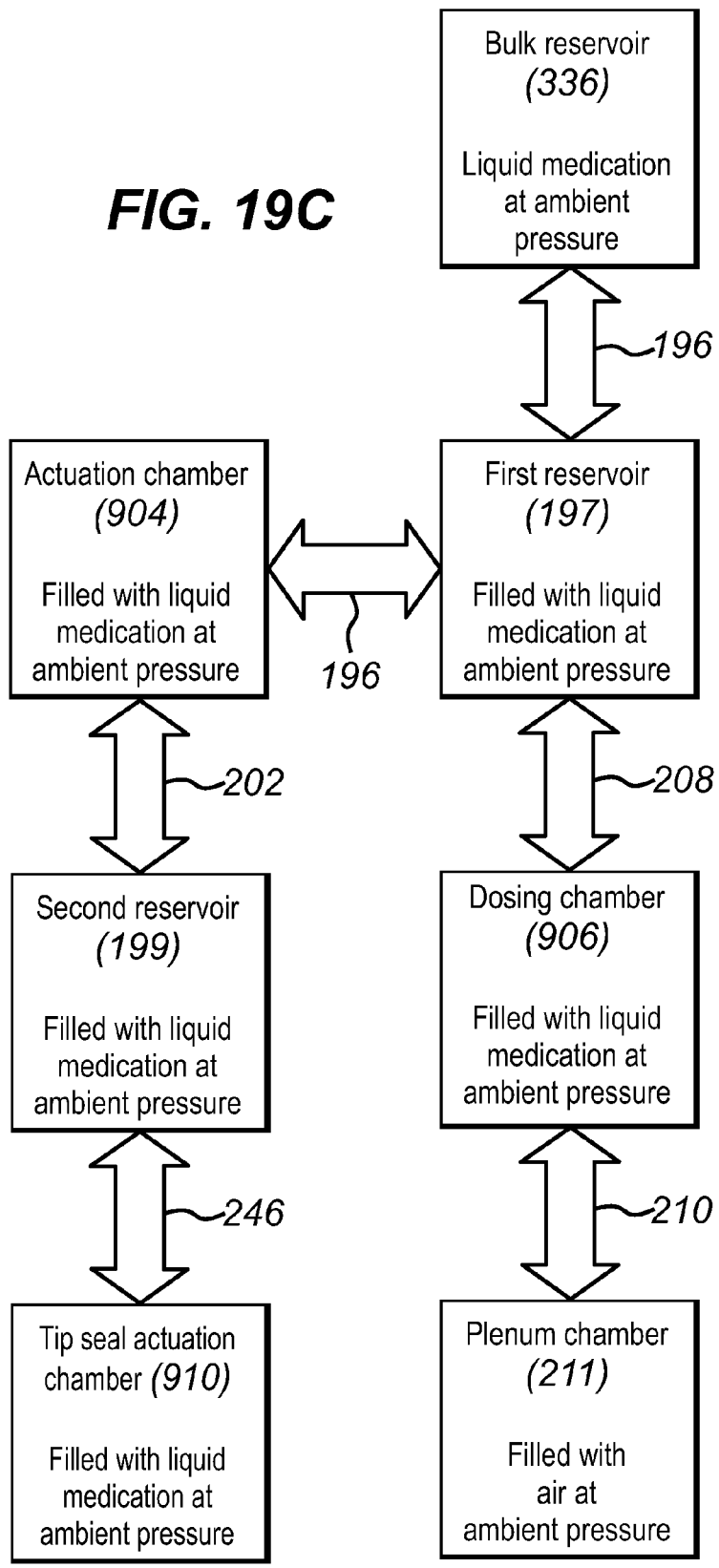

FIGS. 19A, 19B, and 19C show the same views as FIGS. 15A, 15B and 15C in a fourth stage of actuation of the device, also known as the activation phase.

Figure 20A:
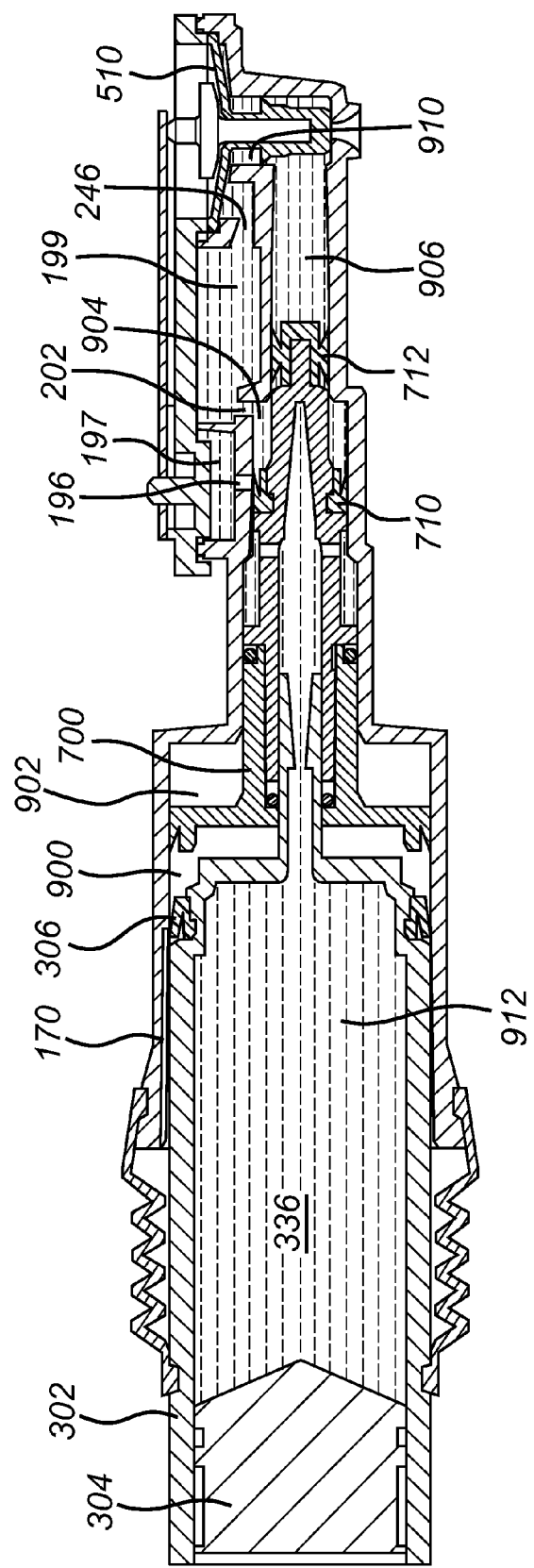
Figure 20B:
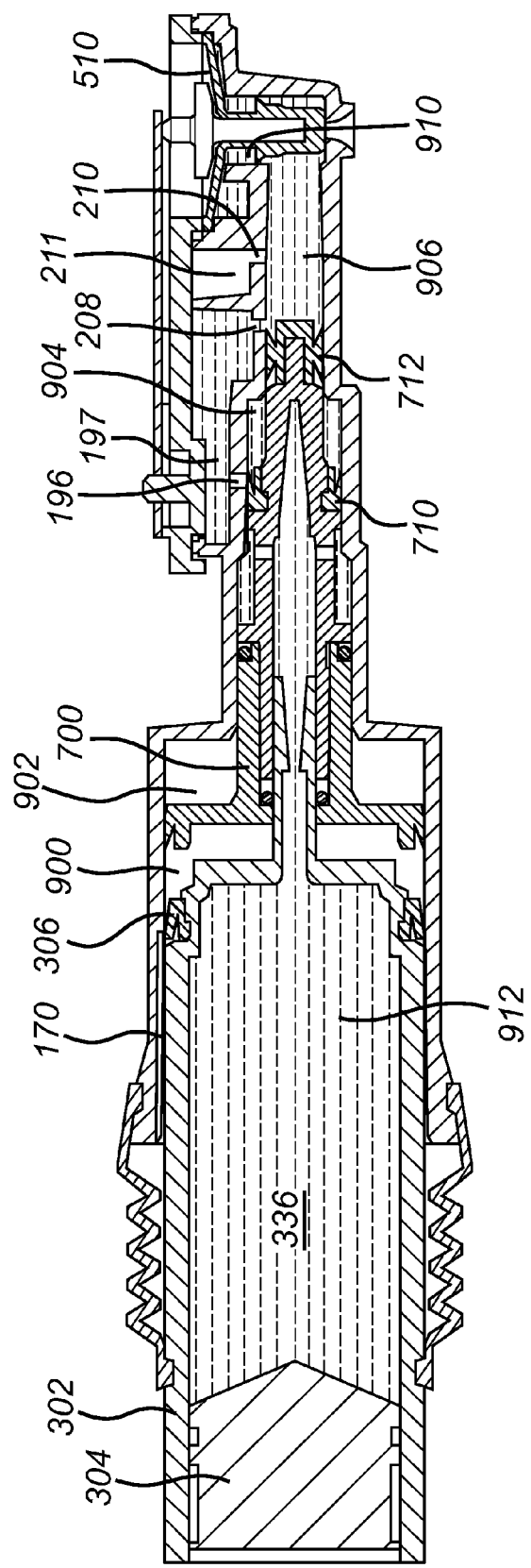
Figure 21B:
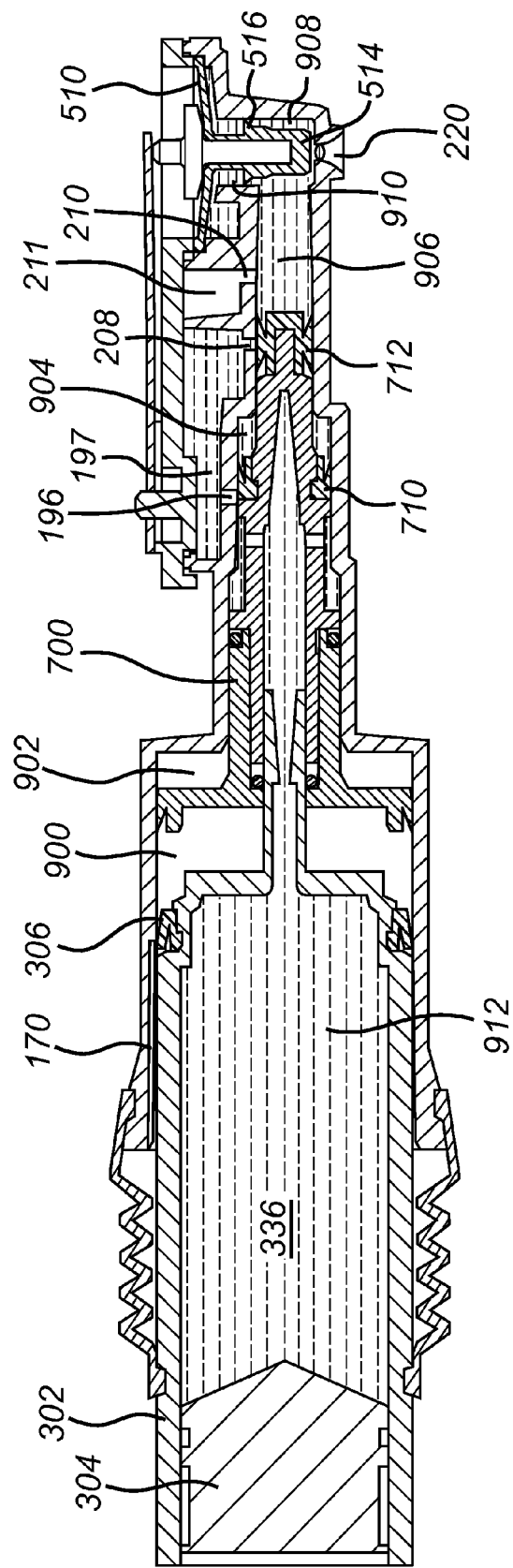
Figure 21C:
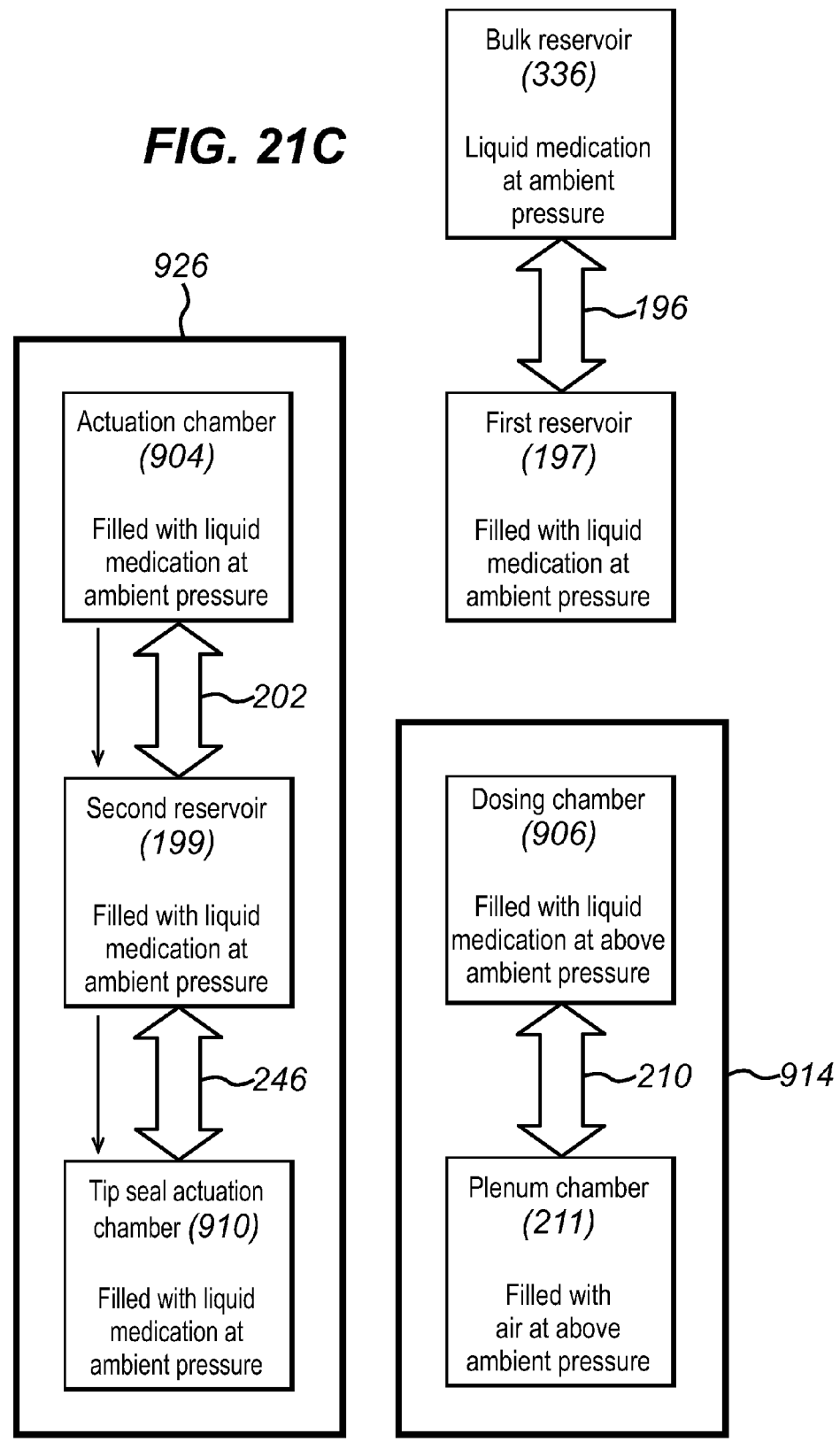

FIGS. 20A, 20B, and 21C show the same views as FIGS. 15A, 15B and 15C a fifth stage of actuation of the device, also known as the fourth priming phase.

FIGS. 21A, 21B, and 21C show the same views as FIGS. 15A, 15B and 15C in a sixth stage of actuation of the device, also known as the first delivery phase.

Figure 22A:
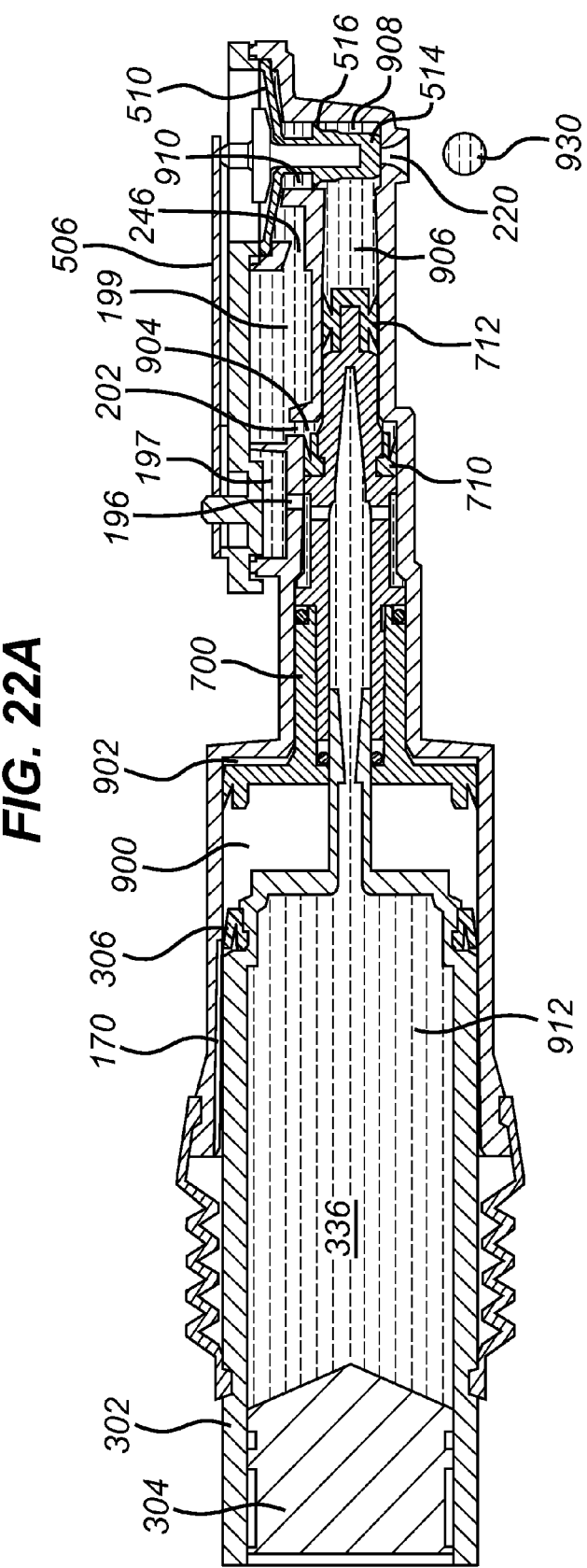
Figure 22B:
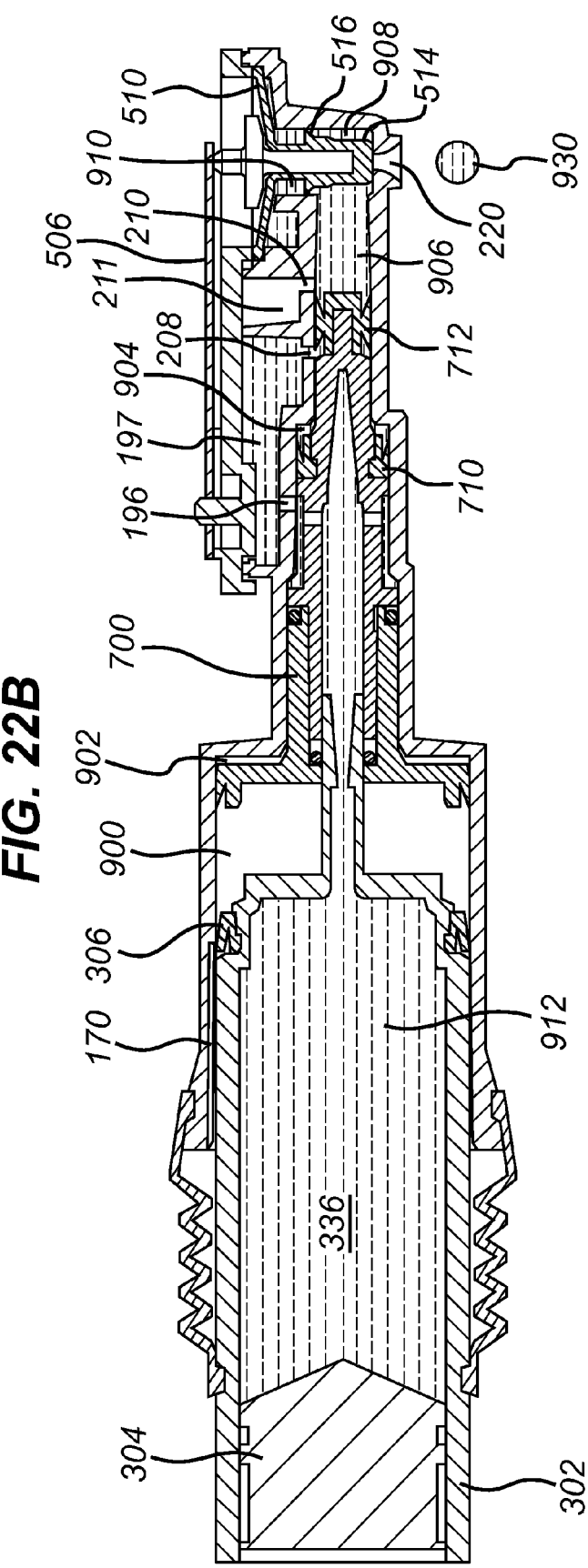
Figure 22C:
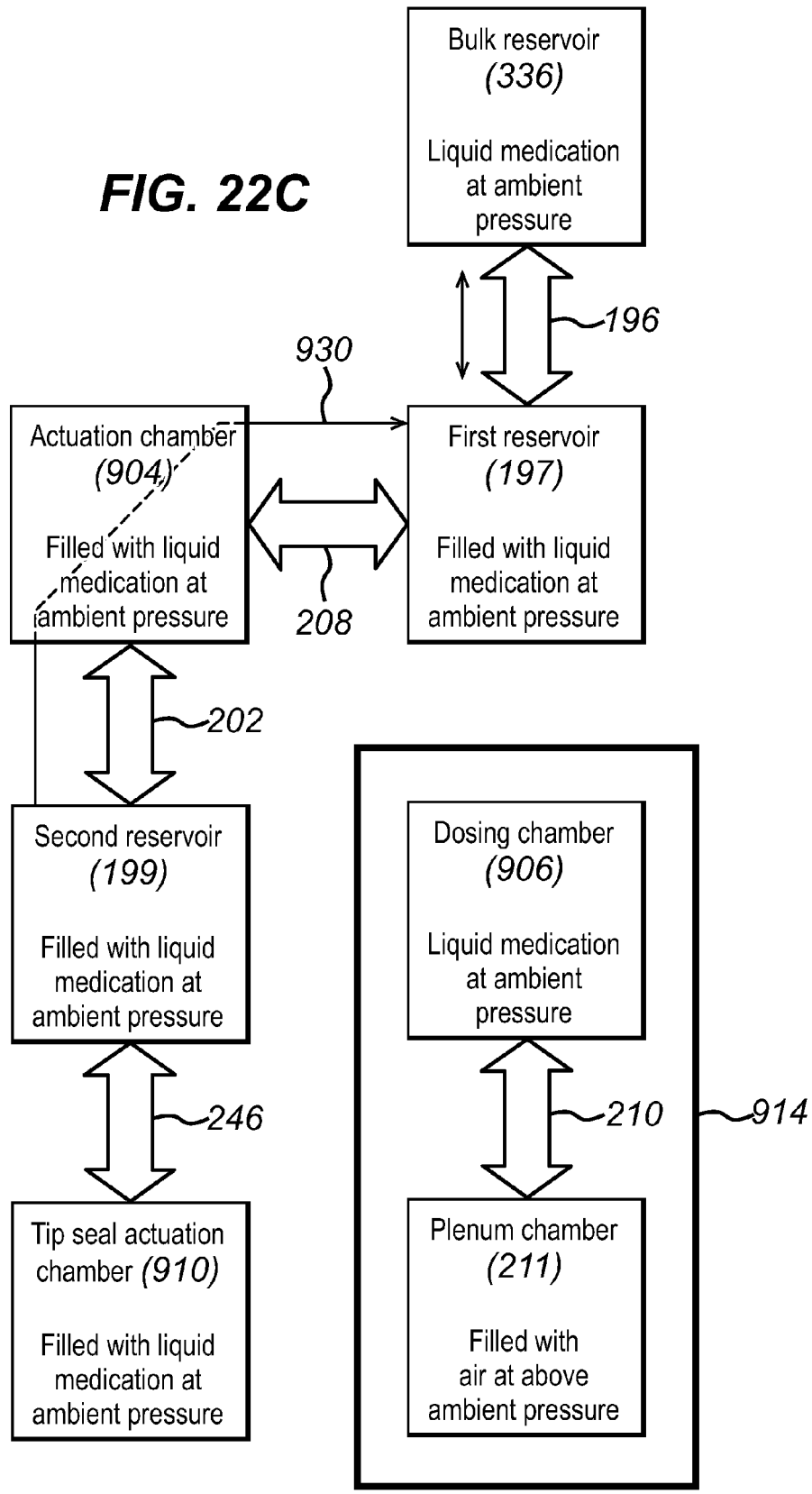

FIGS. 22A, 22B, and 22C show the same views as FIGS. 15A, 15B and 15C in a seventh stage of actuation of the device, also known as the second delivery phase.

NOTE ON FIGURES

FIGS. 1 through 14 FIGS. 1-22 are based upon engineering drawings used for development of the device. Hence the drawings are to scale and representative of the geometry of a dispenser device according to the dispenser, and of an energy storage and commitment mechanism according to the present invention.

DETAILED DESCRIPTION OF THE EXEMPLARY EMBODIMENTS OF THE INVENTION

Figure 1:
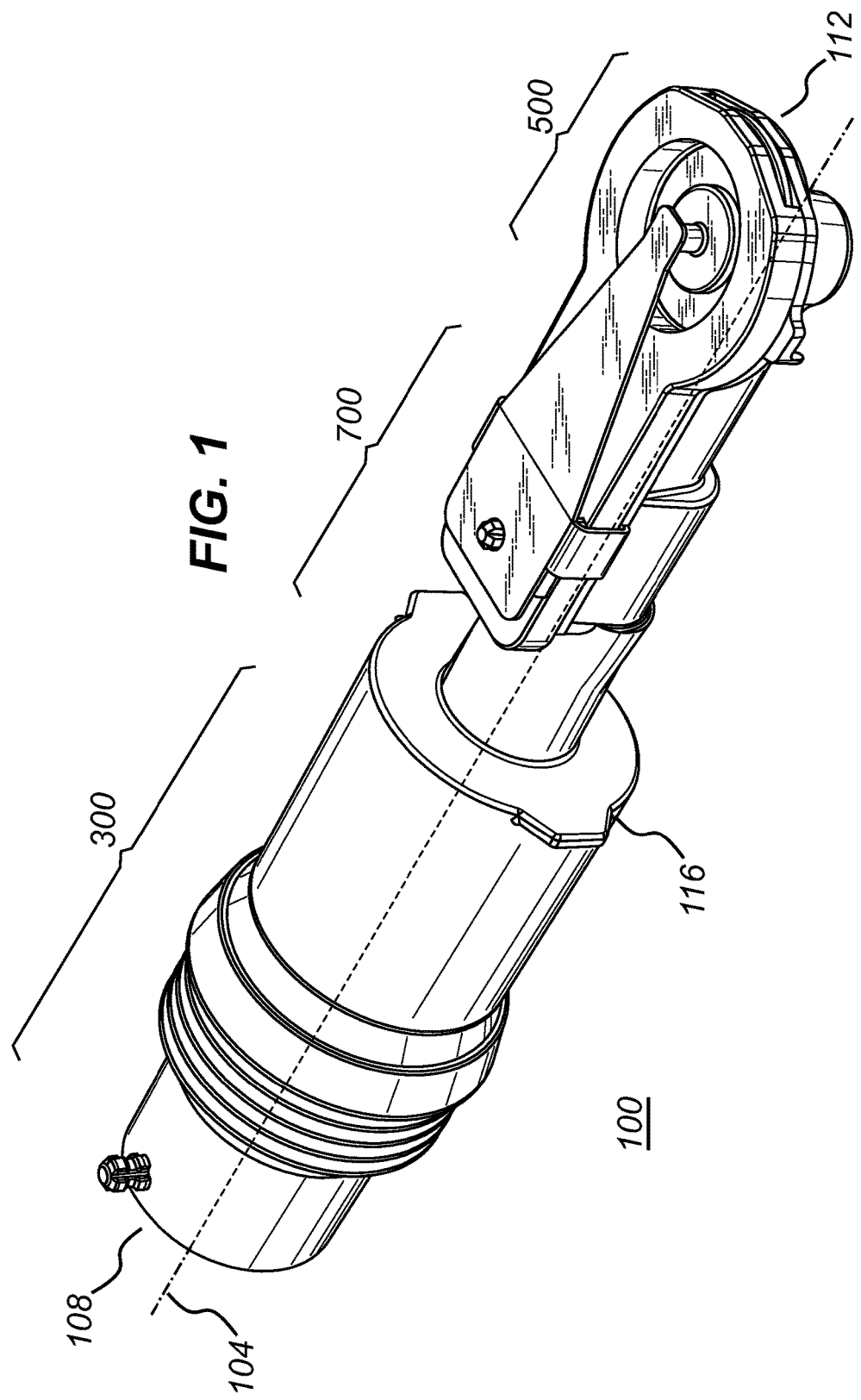
FIG. 1, shows a perspective view of a metered liquid droplet dispenser device, according to the present invention

Referring now to FIG. 1, there is shown a perspective view of a metered liquid droplet dispenser 100, according to the present invention.

The dispenser 100 is elongate in form, and extends along a longitudinal axis 104, from a proximal first end 108 to a distal second end 112. For the purposes of the description, the longitudinal axis 104 will also be referred to as the horizontal axis 104.

A reservoir assembly 300 is provided at the first end 108 of the dispenser 100, and a nozzle assembly 500 is provided at the second end 112 of the dispenser 100. An intermediate assembly 700 is provided between the reservoir assembly 300 and the nozzle assembly 500.

Exploded View & Section of Assembly

Figure 2:
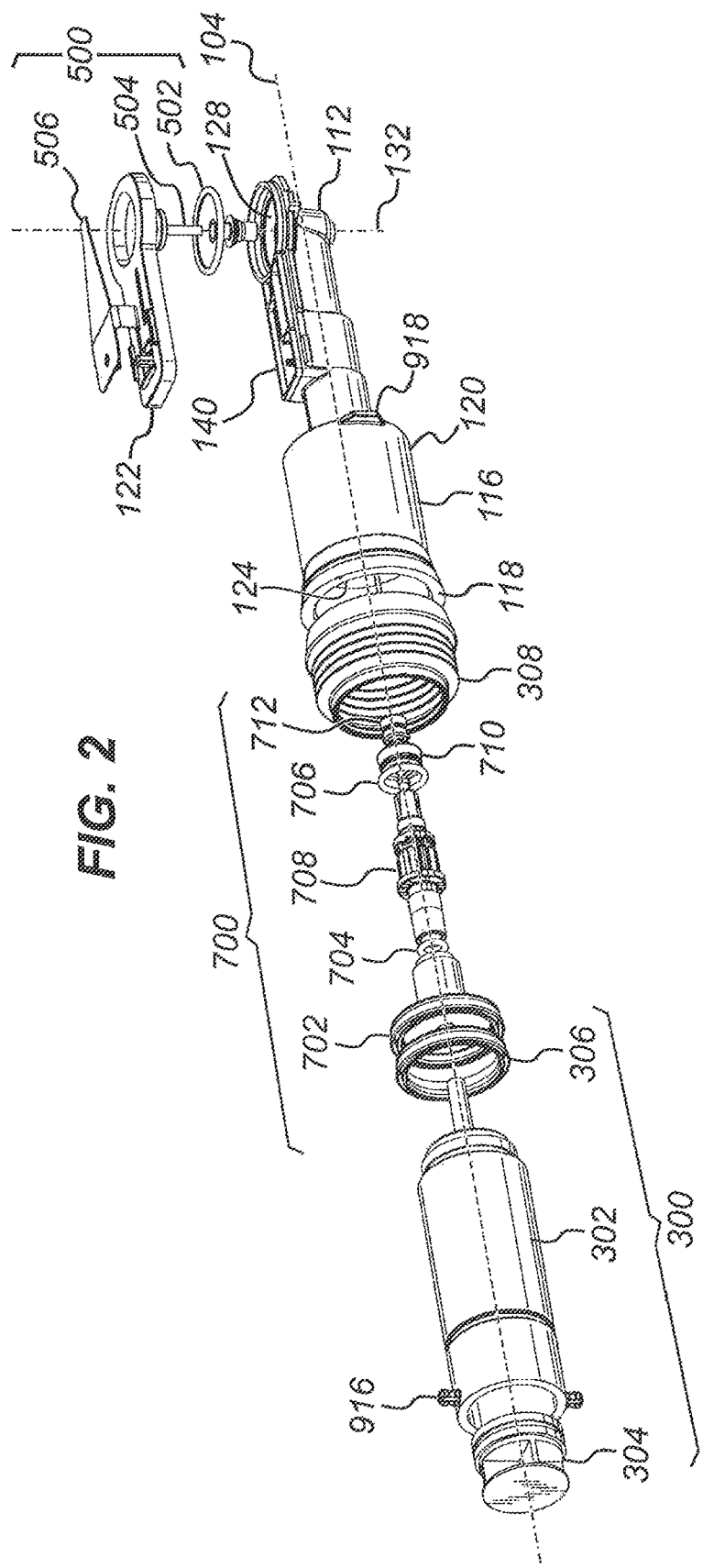
FIG. 2 shows an exploded view of the device of FIG. 1.
Figure 3:
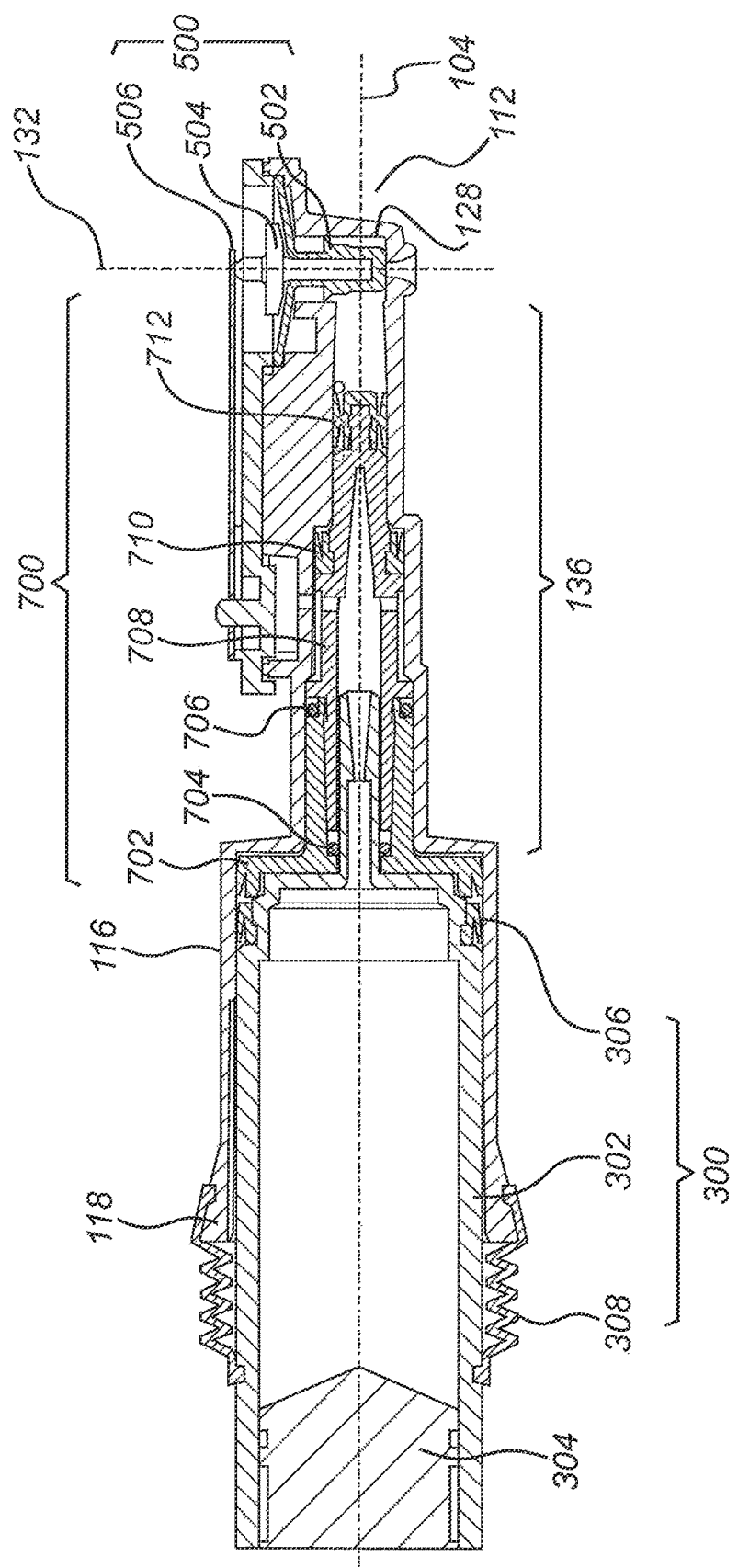
FIG. 3 shows a section view of the assembled device 100 of FIG. 1, sectioned in a vertical plane which passes through a longitudinal axis of the device.

An overview of the device 100 will now be given with reference to FIGS. 2 and 3; FIG. 2 shows an exploded view of the dispenser 100 of FIG. 1. FIG. 3 shows a section view of the assembled dispenser 100 of FIG. 1, sectioned in a vertical plane which passes through the longitudinal axis 104 of the device 100.

The device comprises a housing 116 which extends along the longitudinal device axis 104 from a first housing end 118 to a second housing end 112. The second end 112 provides the distal end 112 of the device 100.

The housing 116 comprises a housing main body 120 and a housing lid 122. The lid 122 is joined to the body 120 at its second end 112. The lid 122 and body 120 are preferably joined by continuous laser welding to provide a housing assembly 116 of effectively unitary construction. This eliminates potential ingress paths for contaminants into the assembled device 100.

Reservoir Assembly

The first end 118 of the housing 116 is adapted to slidably receive a reservoir assembly 300 in a first part of stepped bore 124 which extends along the longitudinal axis 104 of the housing 116. The reservoir assembly 300 comprises a hollow drive piston 302, a reservoir plug 304 and a reservoir vacuum seal 306.

Cylindrical bellows 308 seal the interface between the drive piston 302 and the housing 116 whilst accommodating relative motion between the piston 302 and housing 116.

Nozzle Assembly

The second end 112 of the housing 116 is provided with a through nozzle bore 128 which extends along a vertical axis 132, perpendicular to the longitudinal axis 104. The bore 128 slidably receives a nozzle assembly 500 comprising a tip seal 502 and tip seal piston 504. The nozzle assembly 500 further comprises a leaf spring 506 which is mounted to the exterior of the housing 116 and bears upon the tip seal piston 504 to urge it into contact with an internal sealing face of the housing 116, such that the tip seal is biased against an outlet orifice to seal it at rest.

Intermediate Assembly

The housing 116 is adapted at an intermediate region 136, located between the first end 118 and second end 112, to slidably receive the intermediate assembly 700. The assembly 700 comprises a vacuum seal 702, a first O-ring 704, a second O-ring 706, a master piston 708, an actuation pump seal 710 and a dosing pump seal 712.

Overview—Function

Briefly, the reservoir assembly 300 stores a number of doses of a liquid medication in bulk, and also provides a reciprocable actuator for the input of actuation energy into the device 100.

The nozzle assembly 500 comprises a nozzle outlet which provides a microbial barrier seal in a closed state, and which can be repeatedly cycled from this closed state to an open state in order to dispense multiple metered doses of the liquid medication.

The intermediate assembly 700 interacts with the nozzle assembly 500 to provide a dosing/metering system, which delivers a metered dose of liquid to the nozzle assembly 500, and an actuator system, which actuates the nozzle assembly 500 to cycle the nozzle between its closed state and its open state to allow the metered dose to be expelled/released as a droplet. Both systems preferably use the same liquid medication to minimise the risk of contamination. The volume of both systems, particularly the actuator system, is minimised in order to reduce the amount of liquid that is left unusable when the device has delivered a predetermined number of doses.

The use of a separate dosing/metering system and actuation system enables the tip seal to be opened at a liquid pressure which is independent of the liquid pressure of the expelled dose. This allows the metered dose to be expelled at low pressure, improving droplet formation and allowing very good control of droplet separation from the device.

The intermediate assembly 700 interacts with the reservoir assembly 300 and the nozzle assembly 300, to provide a number of functions. The intermediate assembly 700 and reservoir assembly 300 interact to provide a piston pump, which expands a sealed chamber to store energy, and a release mechanism for the release of this energy to operate the dosing/metering system. These ensure that a guaranteed level of energy is available to the dosing/metering system and actuation system, and further allows control of the manner in which this energy is delivered to these systems. This further allows improved droplet formation and good control of droplet separation from the device.

These features will be explained in more detail below.

DETAILED DESCRIPTION

Housing

Figure 4:
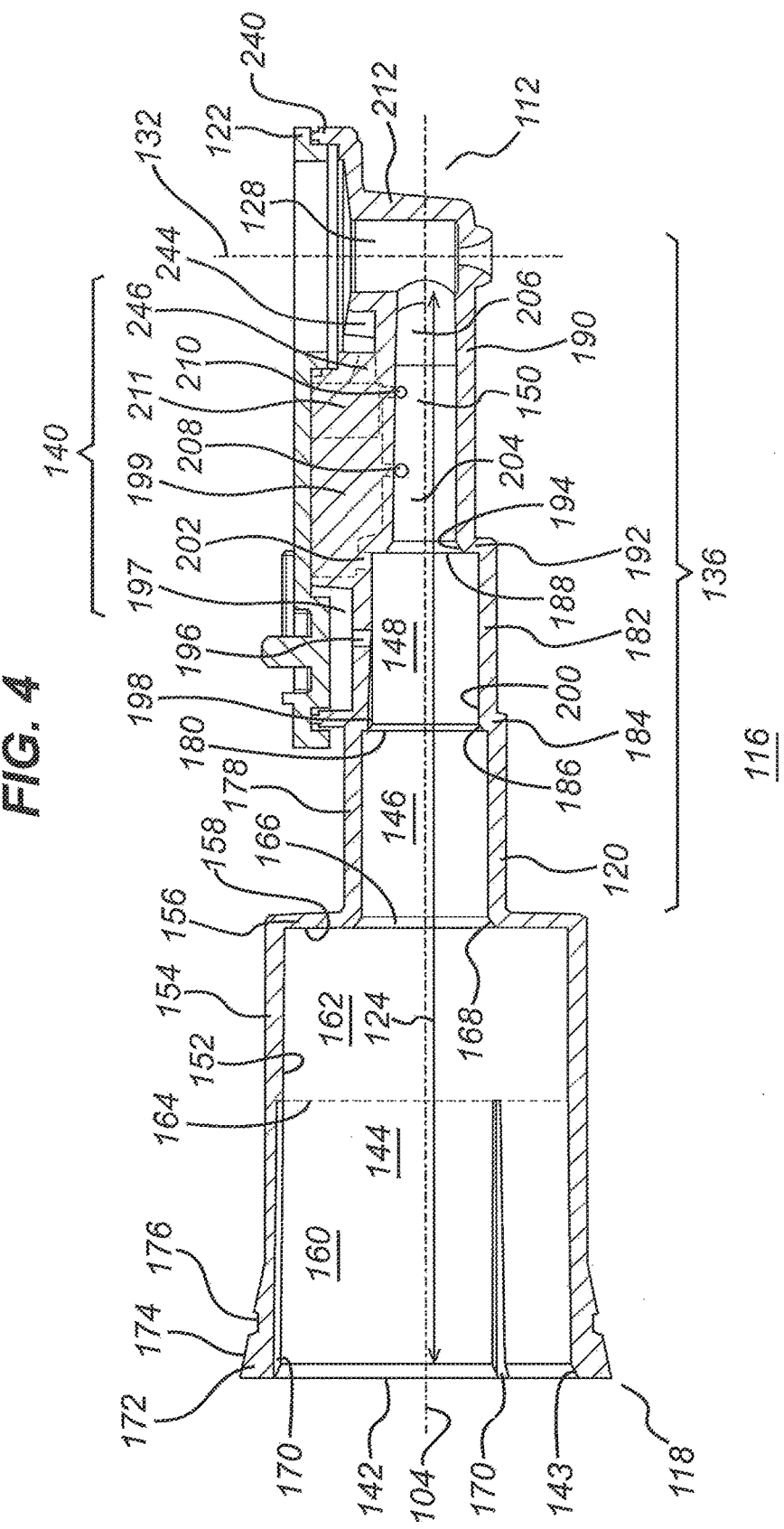
FIG. 4 shows a view on the same section of FIG. 3 showing only the device housing; the rest of the device being omitted for clarity.
Figure 5:
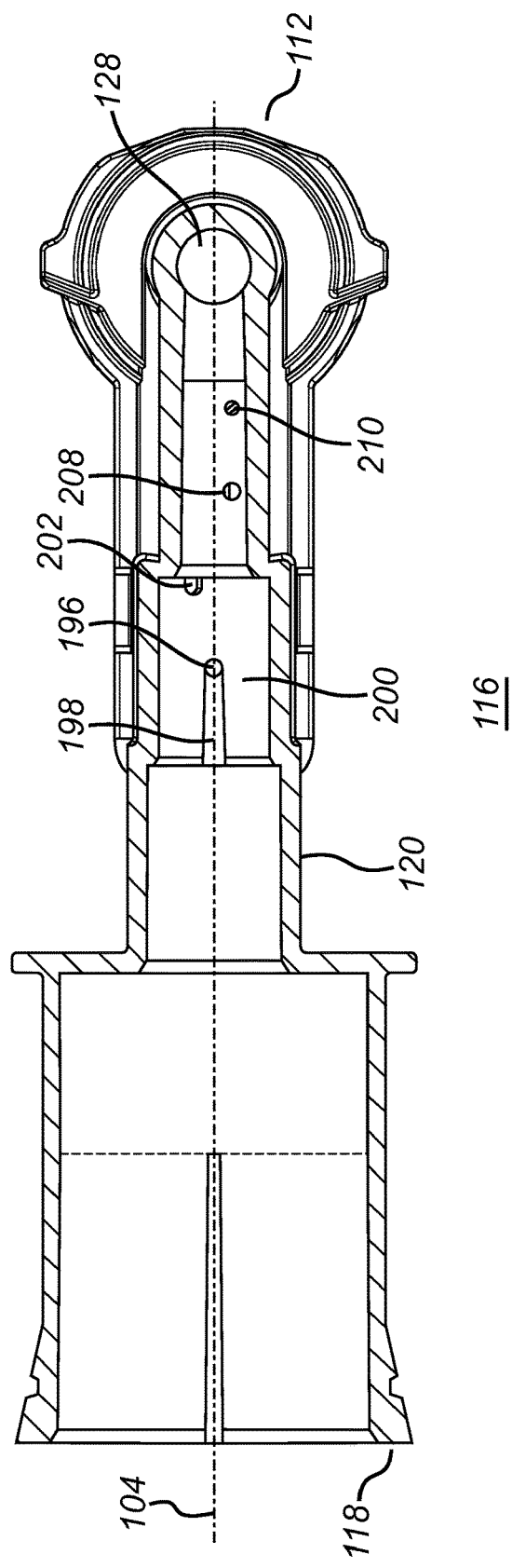
FIG. 5, shows a view from below the device housing of FIG. 3, on a horizontal section through the longitudinal device axis.
Figure 6:
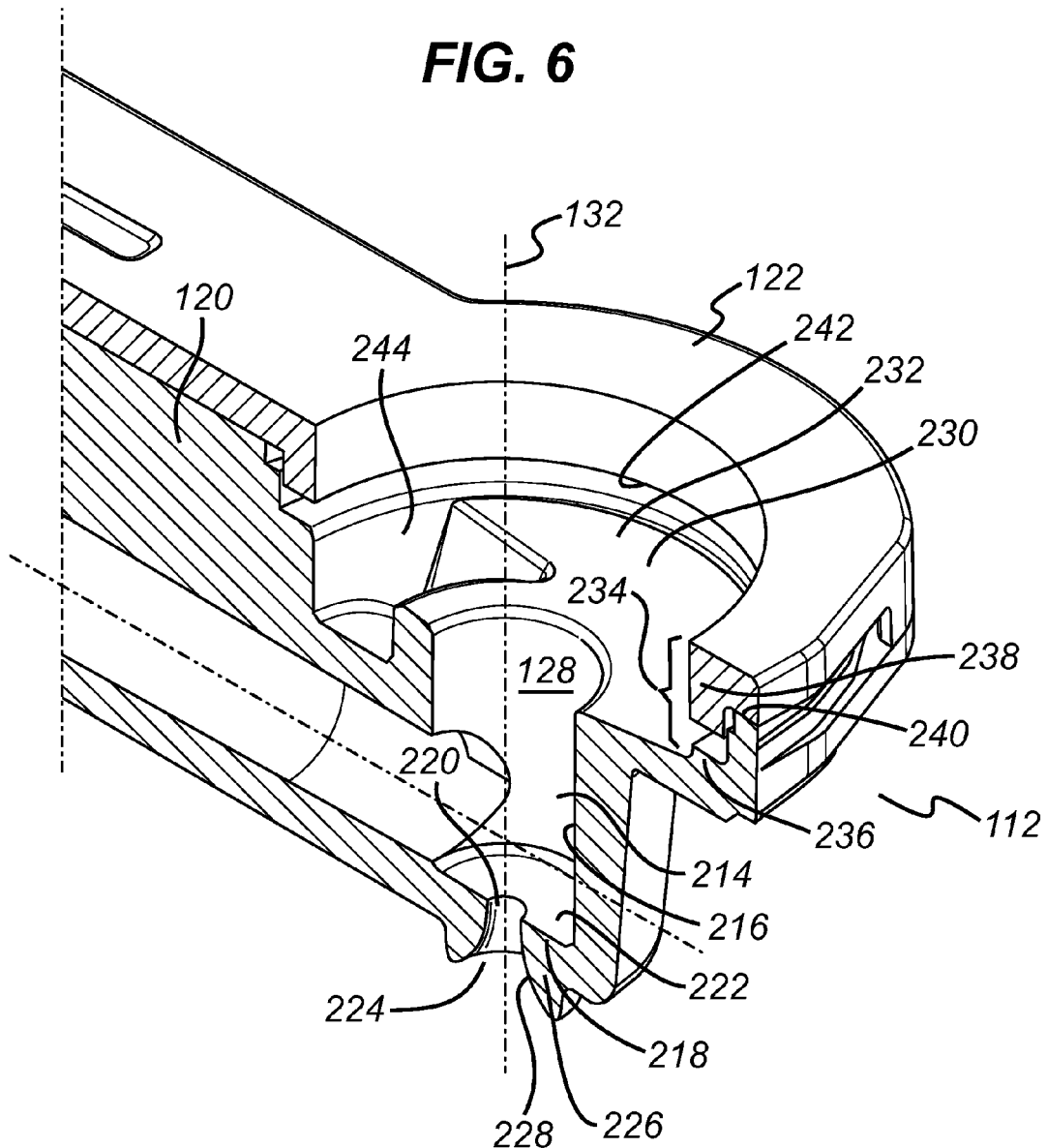
FIG. 6 shows an isometric view on the sectioned housing assembly of FIG. 4, and in particular, a second end of said assembly.

The component parts of the various sub assemblies 300, 500, 700 are received within a device housing 116. Referring now to FIG. 4, there is shown a view on the section of FIG. 3 showing only the housing 116; the rest of the device 100 is omitted for clarity.

The housing 116 can be said to comprise three main features, the previously described stepped longitudinal bore 124 and vertical nozzle through bore 128, and a hydraulic manifold 140, located above the longitudinal bore 124 in the intermediate housing region 136.

Stepped Bore

The main body 120 of the housing assembly 116 defines the stepped bore 124 which extends from a housing inlet 142, formed in the housing body 120. A circumferential chamfer 143 is provided about the inlet 142 which provides a tapered entrance to the stepped bore 124.

The stepped bore 124 extends, coaxial to the longitudinal device axis 104, from the first housing end 118, to join the through-bore 128 which houses the nozzle assembly 500. The stepped bore 124 comprises four coaxial bores 144, 146, 148, 150 arranged in series The bores 144, 146, 148, 150 are arranged in order of descending diameter with the largest diameter bore located at the first housing end 118.

First Bore

The first bore 144, also known as the drive piston housing 144, is defined by the internal surface 152 of a first annular wall 154 which extends generally parallel to the longitudinal device axis 104, from the inlet 142 to a planar end wall 156 which defines the distal end 158 of the bore 144.

The first bore 144 comprises a first frustoconic subsection 160 and a second cylindrical subsection 162 arranged in series.

In more detail, the first, frustoconic subsection 160 has a taper of about 2° inclusive i.e. diametrically opposed surfaces of the bore defined an angle between them of about 2°. The second "cylindrical" section has a taper of about 0.5° inclusive.

The frustoconic portion 160, also known as the commitment portion 160, extends from the inlet 142 to adjoin the cylindrical subsection 162 at an annulus 164 which will be referred to as the commitment annulus 164. The diameter of the frustoconic bore 160 tapers inwards from a maximum diameter at the inlet 142 to the commitment annulus 164. This taper enables the bore 144 to be readily manufactured via injection moulding, allowing withdrawal of the moulding tool after the housing body 120 has been formed.

The cylindrical subsection 162, also known as the major vacuum bore 162, has extends from the commitment annulus 164 to the distal end 158 of the bore 144. The bore 162 tapers inwards very slightly from the commitment annulus 164 to the distal end 158 with an included angle of about 0.5°. This taper enables the inner surface 152 to provide a good sealing surface for engagement with the reservoir assembly 300, whilst still allowing the housing body 120 to be formed by injection moulding.

The distal end wall 156 of the bore 144 is provided with a through hole 166 which communicates with the adjoining second bore 146. The end wall 156 is provided with a circumferential chamfer 168 about the through hole 166 to provide a tapered lead-in.

Three axially directed inlet flutes 170, only two of which are visible in FIG. 4, are set into the internal surface 152 of the frustoconic bore 160. The flutes 170 extend axially from the inlet 142 to the commitment annulus 164 i.e. along the full axial length of the frustoconic bore 160, and are equispaced about the circumference of the bore 144. The flutes 170 each comprise a constant depth groove, which tapers from a maximum width at the inlet 142 to a minimum width at the commitment annulus 164, again for ease of manufacture by injection moulding.

The first annular wall 154 is locally thickened about the housing inlet 142 to provide an annular buttress 172. The outer surface 174 of the annular buttress 172 is locally relieved to define an annular groove 176 for receiving a first end of the bellows 308.

Second Bore

The second bore 146, also called the minor vacuum bore 146, is cylindrical and extends from the distal end 158 of the first bore 144 and is defined by a second annular wall 178. The wall 178 extends from the first bore end wall 156 to a distal end 180 which adjoins a third annular wall 182 via a first annular step 184. The bore tapers inwards with an included angle of about 0.5° to provide a good sealing surface for intermediate assembly 700, whilst allowing manufacture of the housing body 120 by injection moulding. The annular step 184 is provided with a circumferential chamfer 186 which provides a tapered entry to the third bore 148 which adjoins the second bore 146.

Third Bore

The third bore 148, also called the actuation bore 148, is cylindrical and defined by the third annular wall 182. The bore extends from the distal end 180 of the minor vacuum bore 146 to a distal end 188 which adjoins a fourth annular wall 190 via a second annular step 192. The bore tapers inwards with an included angle of about 0.5° over this distance.

The second annular step 192 is provided with a circumferential chamfer 194 which provides a tapered entry to the fourth bore 150, which adjoins the third bore 148.

A through whole 196, also known as the transfer conduit 196, is provided in the wall 182 of the third bore 148 at a position directly above the longitudinal axis 104, separated axially from the distal end 180 of the second bore 146. The conduit 196 allows two-way communication between the third bore 148 and a first reservoir 197 of the hydraulic manifold 140.

An axial flute 198, also known as the bypass flute 198, is set into the inner surface 200 of the bore wall 182, and extends between the annular step 184 at the start of the bore 148, and the conduit 196. This flute 198 is more clearly shown at FIG. 5, which shows a view from below the housing assembly 116 on a horizontal section through the longitudinal device axis 104.

Referring back to FIG. 4, a second through hole 202, also called the actuation conduit 202 is shown in dashed outline. The actuation conduit 202 is provided in the wall 182 of the third bore 148 at a position next to its distal end 188. The conduit 202 allows communication between the actuation bore 148 and a second reservoir 199, also shown in dashed outline, of the intermediate assembly 700. The conduit 202 is oriented vertically, but offset from the longitudinal axis 104 of the device 100, as can be seen more clearly with reference to FIG. 5.

Fourth Bore

The fourth bore 150 also called the dosing bore 150, extends from the distal end 188 of the actuation bore 148 to meet the through-bore 128 located at the second housing end 118. The bore 150 is defined by the fourth annular wall 190 which extends from the stepped transition 192 provided at the distal end of the third bore. The bore 150 comprises a first cylindrical subsection 204, with a taper of about 0.5° included, and a second frustoconic section 206, with a taper of about 2° included, in series. The second subsection 206 tapes inwards, from the conjunction of the two sub-bores 204, 206, until it joins the through bore 128, at the second housing end 112.

A third through hole 208, also called the control conduit 208, shown in dashed outline, is provided in the annular wall 190 of the dosing bore 150. The conduit 208 extends vertically upwards from the bore 150 into the first reservoir 197, and is axially spaced from the distal end 188 of the actuation bore 148. The conduit 208 lies in front of the section of FIG. 4, offset from the longitudinal axis 104 in the horizontal plane.

Referring back to FIG. 4, a fourth through hole 210, also called the plenum conduit 210, is shown in dashed outline. The conduit 210 is provided in the wall of the cylindrical section 204 of the dosing bore 150, and extends vertically upwards to provide a sole communication path between a sealed plenum chamber 211, shown in dashed outline, and the dosing bore 150. The plenum conduit 210 lies in the same plane as the control conduit 208, and is axially spaced therefrom, towards the end of the bore 150. The offset of the control conduit 208 and plenum conduit 210 is shown more clearly at FIG. 5.

Vertical Through Bore for Nozzle Assembly

At the second end 112 of the housing assembly 116, the through bore 128 is defined by a fifth annular wall 212. The structure of the through bore 128 is set forth in more detail at FIG. 6 which shows an isometric view on the sectioned housing assembly 116 of FIG. 4, and in particular, the second end 112 of said assembly.

The through bore 128 comprises a first lower cylindrical section 214 which has an internal surface 216 adapted to slidably receives the tip seal 502 and tip seal piston 504. The bottom of the cylindrical section 214 is terminated by a base 218, which defines an outlet orifice 220. The internal face 222 of the base 218 provides a planar sealing face 222 which abuts the tip seal 502 of the nozzle assembly 500 (not shown) to close the outlet orifice 220. The quality of surface finish of the face 222 is preferably between VDI 3400 no.18 Ra0.80 Rz3.3 and SPI A1 Ra0.025 Rz0.1

The orifice 220 leads to a nozzle 224 which is defined by an annular lip 226. The internal surface 228 of the lip 226 is shaped to form an axisymmetric "flaring bell". This geometry ensures that a liquid passing through the nozzle slows as it moves away from the nozzle orifice 220, promoting stable drop formation.

The top end of the cylindrical subsection 214 opens into a wider upper bore 230. The upper bore 230 comprises a shallow conical base 232, which flares outwards and upwards from the lower cylindrical bore 214 to join a cylindrical annular wall 234. This annular wall 234 comprises a lower annular lip 236 formed in the housing main body 120, and an upper annular lip 238 formed in the housing lid 122. The housing main body 120 and the housing lid 122 are permanently joined about an annular abutment 240, located outside of the annular wall 234, such that the upper and lower lips 236, 238 are held in a spaced relationship to define an annular groove 242 between them which retains and seals, microbially, the tip seal 502 (not shown) when the nozzle assembly 500 is in place.

The shallow conical base 232 of the upper bore 230 is locally relieved in a region located over the dosing bore 150, between the wall of the lower bore 214 and the wall of the upper bore 230, to create a recess 244 known as the actuation follower reservoir 244. This reservoir 244 is linked to the second reservoir 199 of the hydraulic manifold 140 via a horizontal, tapering, conduit 246 shown in dashed outline at FIG. 4.

Hydraulic Manifold

Figure 7:
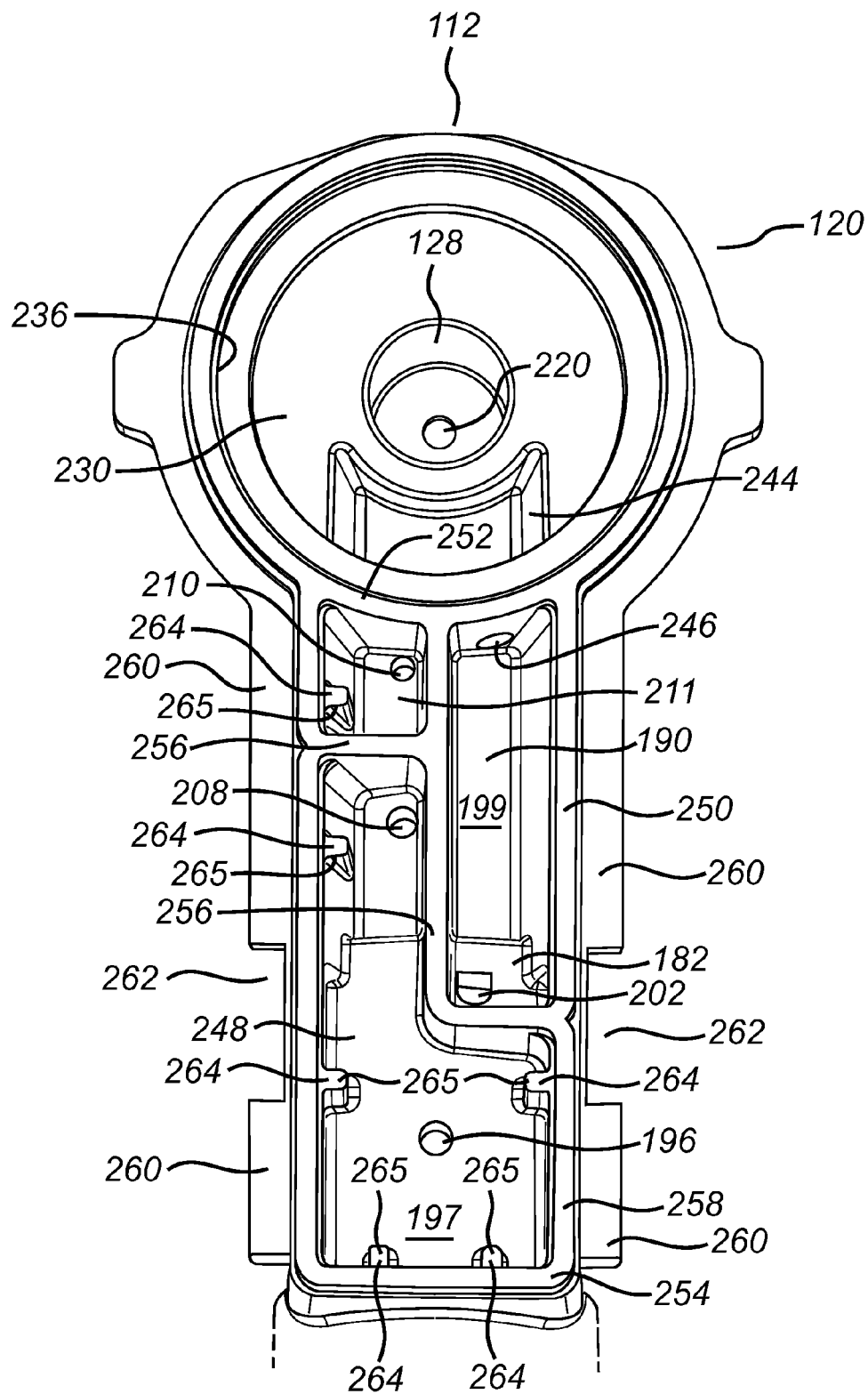
FIG. 7, shows a perspective view on the second end of the housing body.

The construction of the housing hydraulic manifold 140 will now be described with reference to FIG. 4 and also with reference to FIG. 7, which shows a perspective view on the second end 112 of the housing body 120, absent the housing lid 122.

The manifold 140 comprises a basin 248 of rectangular plan, defined by a perimeter wall 250 which projects vertically upwards from the walls 182, 190 of the actuation and dosing bore 148, 150. The same walls 182, 190 provide the base of the basin 248.

The basin extends axially from a first end 252 which abuts the upper bore annular lip 236, to a distal end 254 which sits above the stepped transition 184 between the minor vacuum bore 146 and the actuation bore 148.

A dividing wall 256 divides the basin 248 into three separate reservoirs; the first reservoir 197, the second reservoir 199 and the plenum chamber 211. The perimeter wall 250 and the dividing wall 256 rise to the same height above the device axis 104 to define a planar upper surface 258 that the housing lid 122 abuts. The three reservoirs, 197, 199, 211 are arranged so that each has a perimeter which lies as close as possible to a plane passing vertically through the axis 104 of the housing 116. This allows the vertical holes 196, 202, 208, 210 which pass between the manifold 140 and the stepped bore, to be located as close the 12 o'clock position as possible, i.e. to lay vertically above the axis 104 with minimal lateral displacement. This ensures that where they meet the bore 124, the intersection creates the minimal disruption to the internal surface of the bore 148, 150. This ensures minimal distress to any seals of the intermediate assembly 700 that pass over the holes.

A longitudinally extending flange 260 is provided on opposing sides of the basin 248. The flange is interrupted by a rectangular cut-out 262 located towards the distal end 254 of the basin.

The flange 260 continues around the lower annular lip 236 of the upper part 230 of the through bore 128, except at the first housing end 112, where it is locally relieved.

A number of flat-topped buttresses project from the perimeter wall within the first reservoir 197 and the plenum chamber 211. These extend to an abutment plane which sits beneath the planar upper surface 258 of the perimeter wall and dividing wall 256.

Housing Lid

Figure 8:
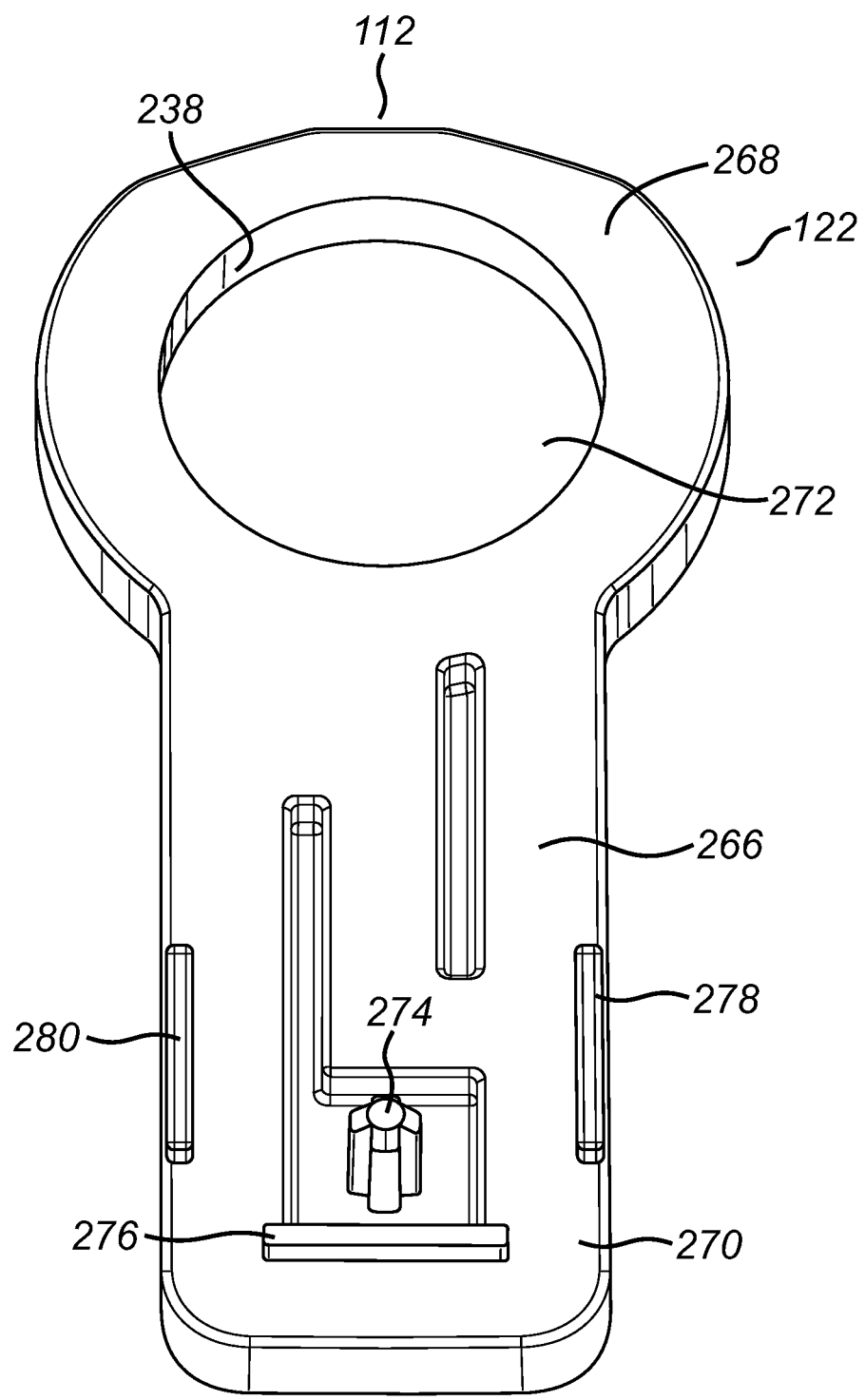
FIG. 8 shows a perspective view of a housing lid for the device from above.
Figure 9:
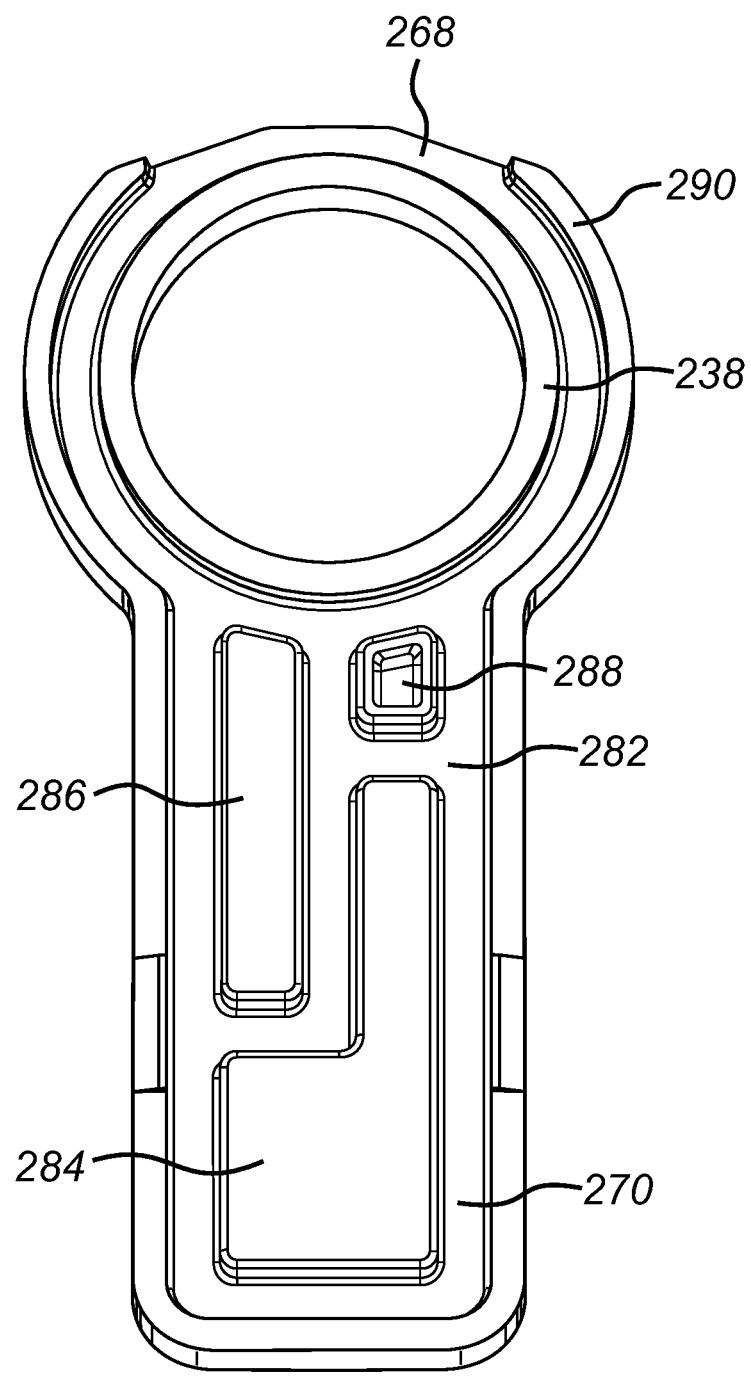
FIG. 9 shows a perspective view of the housing lid from below.

FIG. 8 shows a perspective view of the housing lid 122 from above, and FIG. 9 shows a perspective view of the housing lid 122 lower from below, i.e. as would be seen from within the hydraulic manifold 140 of the assembled housing 116.

The housing lid 122 defines a planar upper surface 266 comprising an annular collar 268, for location at the second housing end, and a distal planar basin cap 270, configured to overlap the perimeter 250 of the basin 248 of the housing body 120.

The annular collar 268 defines a circular cut out 272 which provides, at an inner circumferential surface thereof, the upper annular lip 238 of the vertical through bore 128.

An upstanding peg 274, of cruciform cross-section projects from the upper surface 266 to locate the leaf spring 506 (not shown) of the nozzle assembly 500. Three upstanding walls 276, 278, 280, stand proud of the basin cap 270 to provide a supporting surface for the spring and ensure that it is spaced away from the housing lid 122. The first traverse wall 276 traverses the lid at the distal end relative to the collar 268 while the second and third axial wall, 278, 280 run along either side of the basin cap, to lie adjacent the flange cut-outs 262 provided to the housing body 120 in the assembled state of the lid 122 and body 120.

With reference to FIG. 9, the underside 282 of the basin cap 270 has three plugs 284, 286, 288, which project downwards from the cap. The first plug 284 is shaped to fit within the first reservoir 197 and to abut the buttresses 264 provided to the basin perimeter wall 250. The second plug 286 is shaped to fit within the second reservoir 199. The third plug 288 is shaped to fit within the plenum chamber 211 and to abut a buttress 264 provided to the perimeter wall 250 within the plenum chamber 211. The plugs 284, 286, 288 and buttresses 264 locate the lid 122 relative to the housing body 120 when placed together prior to joining, preferably by laser welding. Furthermore, the plugs 284, 286 serve to reduce the volume of the first and second reservoirs 197, 199, which contain liquid, to reduce the amount of liquid that is left unusable when the device has delivered a predetermined number of doses. In particular, the use of the plugs 284, 286 enables small volume reservoirs 197, 199 to be reliably manufactured with an injection moulding process.

A downward projecting perimeter wall 290 is provided around the basin cap 270 and about part of the annular collar 268. When the cap 270 is assembled to the basin 248, the wall 290 abuts the flange 260 of the housing body 120.

When the cap 270 is permanently attached to the basin 248, it seals the reservoirs 197, 199 and plenum chamber 211 such that communication with them can only take place via the vertical holes 196, 202, 208, 210, and horizontal conduit 246 already discussed. The joining process ensures that the seal between the housing body 120 and housing lid 122 can maintain an internal pressure which is above, or below, the ambient pressure external to the device 100.

The housing main body 120 is formed from polypropylene as a single item, preferably by injection moulding. Similarly, the housing lid 122 is formed from polypropylene, preferably by injection moulding.

In the present embodiment, the housing lid 122 is laser welded to the housing main body 120. To aid this process, the main body 120 material is dosed with a laser absorbing material, and the lid material is not. This allows laser energy to pass through the lid before being absorbed by the dosing material. This ensures localised heating of the body 120 material so that the lid 122 and housing 120 fuse to one another. In the present example, the dosing material is about 0.2% carbon by weight.

The perimeter wall 250, dividing walls 256, and lower annular lip 236 of the housing main body all extend above the joining plane 265 formed by the upper surface of the abutments 264, formed in the housing main body 120. The material above the joining plane provides a consumable region of material for continuous laser welding.

In more detail, during joining of the housing body 120 to the housing lid 122, the laser is directed vertically downwards upon the upper surface 266 of the lid 122 directly over the joining surfaces 236, 250, 256 of the housing body 120. The laser passes through the lid 122 due to the absence of absorbing material therein and is subsequently absorbed by the consumable region of the housing body 120 which melts. As it does so, the housing lid 122 settles downwards until it rests upon the buttresses 264, which are not irradiated by the laser.

Hence the buttresses and particularly the upper surface of the buttresses enable a good control of the overall height of the joined housing 116. This is important as excess variation in the height of the joined housing 116 would otherwise lead to inconsistencies in the performance of the leaf spring 506 and inconsistency with sealing of the nozzle orifice 220.

Reservoir Assembly

Figure 10:
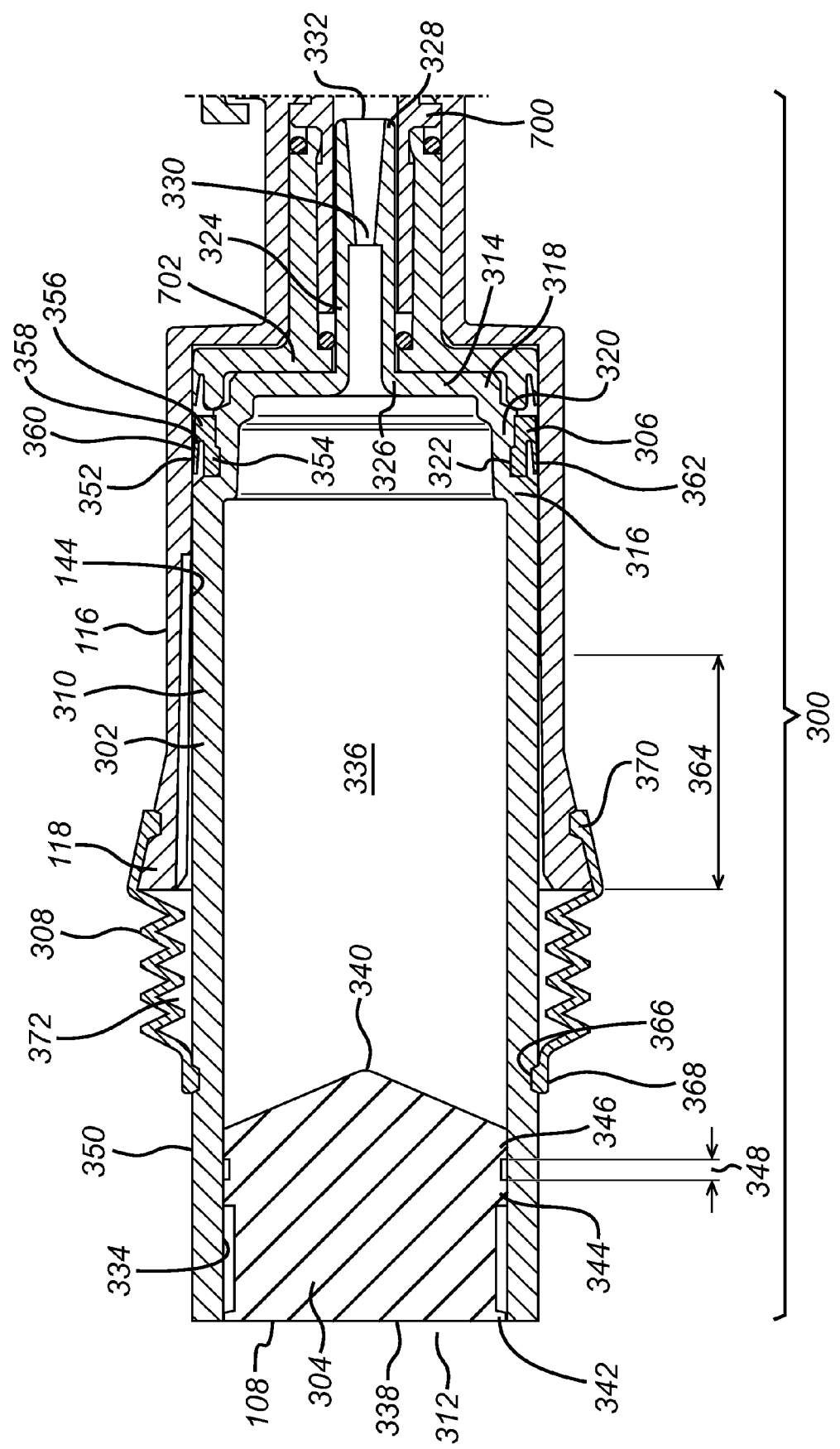
FIG. 10, shows a view on a first end of the sectioned device of FIG. 3 in order to show the first end in more detail.

FIG. 10, shows a view on the first end 108 of the sectioned device of FIG. 3 in order to show the reservoir assembly 300 in more detail.

The hollow drive piston 302 of the reservoir assembly 300 is adapted to be slidably mounted within the drive piston bore 144 of the housing 116. In the rest state of the device 100 shown at FIG. 10, the drive piston is fully inserted into the drive bore so that it abuts the intermediate assembly 700.

The piston 302 comprises a cylindrical main body section 310 which extends from an open end 312 to a planar bulkhead 314. A first annular shoulder 316 and second annular shoulder 318 provide a stepped transition from the cylindrical body 310 to the outer edge of the bulkhead 314. An annular land 320 between the steps 316, 318 is provided with a groove 322 to captively engage the reservoir vacuum seal 306.

A stem 324 projects from a proximal end 326 at the piston bulkhead 314 to a distal end 328. The stem 324 defines a lumen 330 which extends from the main body 310 to an outlet 332 at the distal stem end 328. The stem 324 and main body 310 are arranged in series, axisymmetric about the longitudinal device axis 104 and, as such, the drive piston 302 can be seen to resemble an open bottle resting on its side.

The open end 312 of the main body defines a circular bore 334 which extends as far as the first annular step 316 and which receives the reservoir plug 304. The end 312 of the main body forms the first end 108 of the assembled device 100.

The interior 336 of the drive piston 302 defines a bulk reservoir cavity 336 which is sealed at the open end 312 by the reservoir plug 304. The cavity 336 holds the majority of liquid medication (not shown) when the device 100 is filled before use. In the present embodiment, the maximum volume of the bulk reservoir 336 is about 5 cubic centimeters.

The plug 304 comprises a cylinder of compliant material, preferably ethylene propylene diene monomer (EPDM) rubber, that extends from a planar base 338 to a conical tip 340 that is received within the drive piston bore 334. The plug 304 is provided with a first annular lip seal 342 adjacent the base and, a second annular lip seal 344 and third annular lip seal 346 towards the tip 340. The second and third seal 344, 346 are horizontally spaced apart by a predetermined distance called the swept distance 348.

The plug 304 and piston 302 are adapted such that the plug 304 is drawn towards the piston bulkhead 314 as liquid is taken from the bulk reservoir 336. In other words, they cooperate to provide a collapsible reservoir, which avoids the creation of headspace, i.e. ullage, and so minimises the creation of sub-ambient pressure within the reservoir 336 which could draw air, and contaminants, into the device 100. An alternative solution, to introduced ambient air into a non-collapsible reservoir also risks introducing contamination into the device.

A further effect of the movable plug 304 is to equalize pressure within the device 100 with the ambient, atmospheric, pressure outside pressure by allowing expansion, of contraction of the bulk reservoir. Fluid is therefore able to flow to or from those internal regions of the device 100 which are in fluid communication with the bulk reservoir 336 as necessary.

The cylindrical outer surface 350 of the main piston body 310 is of a diameter which slidably engages the drive piston bore 144 over the region of the drive piston 302 located within the housing 116. This sliding engagement serves to coaxially locate the piston 302 within the bore 144 to stabilise the reservoir assembly 300 and prevent piston rock. This ensures that the one way vacuum seal 306, of the assembly 300, is stable and functions optimally to provide an air-tight seal at a first sliding sealing interface 352 defined between the reservoir assembly 300 and the major vacuum bore 162 of the drive piston bore 144.

In more detail, the seal 306 is a lip seal 306 which locates in the annular seal groove 322 formed in the land 320. The seal 306 comprises an annular base 354 which is held axially captive within the groove so that the seal 306 moves with the piston 302. A radially upstanding wall 356 projects from the seal base 354, and a lip 358 extends from the diametrically outer edge of this wall 356 towards the end of the piston 312, i.e. away from the piston bulkhead 314, and radially outwards to define a conical sealing surface 360. In the unassembled state, at least a complete annular portion 362 of the conical sealing surface 360 is of greater diameter than the internal surface 152 of the major vacuum bore 162. The lip 358 is compressed radially inwards upon insertion into the drive bore 144 so the seal 306 positively engages the internal surface 152 of the drive piston bore 144 in the assembled rest state of FIG. 10 to provide the seal interface 352. This positive, resilient, engagement of the sealing surface 352 and the internal bore surface 152 accommodates the slight taper provided to the bore 144 during sliding movement of the sealing surface along the bore 146.

The inlet chamfer 168 provided to the housing 116 ensures that the seal 306 is gradually compressed upon introduction into the housing 116 to avoid damage thereto.

The conical geometry of the lip 358, allows some leakage past the sealing interface 352 from the bore distal end 158 in the direction of the inlet 142, but not in the opposite direction.

The reservoir vacuum seal 306 is formed as a single component from low density polyethylene in the present embodiment, preferably by injection moulding.

In use, the drive piston 302 is reciprocated within the drive bore 144 as will be explained in more detail subsequently. As a consequence, an external "swept" region 364 of the piston will cycle from within the bore 144 to a position outside of it and back again. This presents a risk of contamination as the swept surface 364 could be exposed to contaminants while outside the housing 116.

An annular groove 366 is provided at a point on the drive piston 302 which always lies external to the housing 116. This groove 366 retains an annular, lipped, first end 368 of the bellows 308. The second, opposite lipped end 368 of the bellows 308 is retained by the annular groove 176 provided to the housing 120. The bellows 308 provides an axially extendible cover which ensures that the swept region 364 of the piston 302 is not exposed to contaminants. Both lipped ends 368, 370 of the bellows sealingly engage the piston 302 and housing 116 respectively to define a sealed gas reservoir 372 within the bellows 308, which is isolated from the external environment.

Intermediate Assembly

Figure 11:
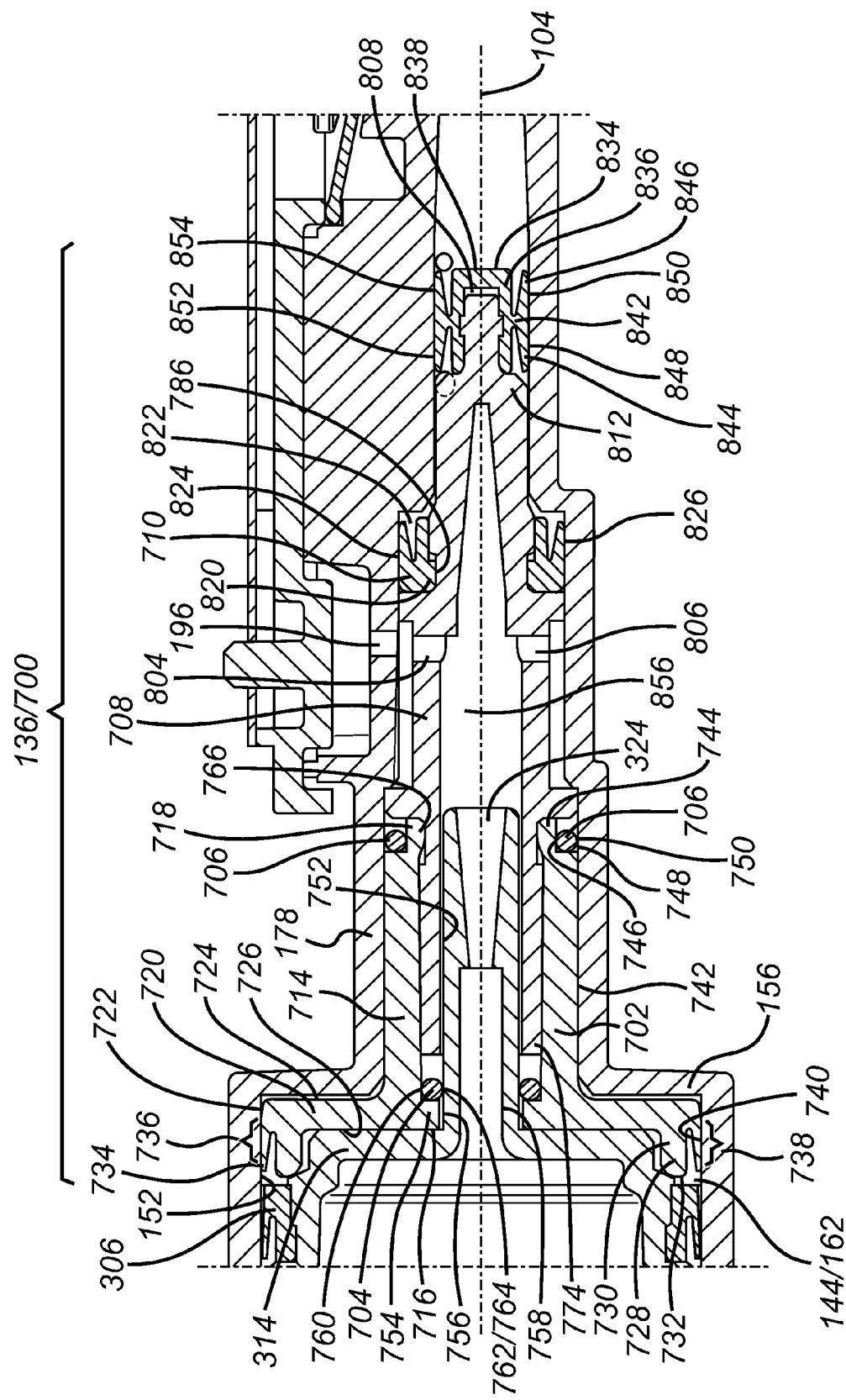
FIG. 11, shows a view on an intermediate region of the sectioned device of FIG. 3 in order to show the intermediate region in more detail.

FIG. 11, shows a view on the intermediate region 136 of the sectioned device 100 of FIG. 3 in order to show the intermediate assembly 700 in more detail.

The intermediate vacuum seal 702 of the assembly 700 comprises an open cylinder 714 which extends from a first free end 716, located within the drive piston bore 144 at rest, to a second end which retains a first end of the master piston 708.

In the rest state shown at FIG. 11, the first cylinder end 716 lies within the major vacuum bore 162, terminating adjacent the end wall 156 of the drive piston bore 144. A radially extending sealing disk 720 extends about the first cylinder end 716 which provides an outer circumferential surface 722 that lies next to the internal surface 152 of the bore 162.

The disk 720 has a planar first face 724 which lies next to the distal end 156 of the drive piston bore 144 and a planar second face 726 which faces away from the distal end 156, towards the first housing end 118.

An annular limb 728 projects from the second disk face 726, coaxial with the longitudinal device axis 104, towards the first end of the bore 144. The limb 728 has a base 730 located inboard of the outer circumferential surface 722, and a distal end 732.

A lip seal 734 extends from the sealing disk edge 722 towards the end of the piston 312, and radially outwards, to define an outer conical sealing surface 736. A complete annular portion 738 of the conical sealing surface 736 is of greater diameter than the internal surface 152 of the vacuum bore 162. The lip 734 is compressed radially inwards by the housing 116 to ensure sealing engagement with the internal surface 152 in the assembled state shown. The inlet chamfer 168 provided to the housing 116 ensures that the seal is gradually compressed upon introduction into the housing 116 to avoid damage thereto.

The positive engagement between the lip seal 734 and the internal surface 152 of the drive piston bore 144 creates a second sliding sealing interface 740 between the sealing disk 720 and the housing 116. The seal acts as a one way valve because of the conical geometry of the lip seal, allowing some leakage past the sealing interface 740 from the first disk face 724 to the second disk face 726, but not in the opposite direction.

The outer surface 742 of the seal 702 is cylindrical, having an included angle of about 0.5° to allow manufacture of the seal by injection moulding 702. The surface 742 is relieved at the second end 718 to provide an annular shelf 744 of reduced diameter for radial location the second O-ring 706, via the internal diameter 746 of the O-ring 706. The shelf 744 urges the external diameter 748 of the O-ring against the minor vacuum bore wall 178 to create a third sealing interface 750, between the bore 146 and the intermediate vacuum seal 702. The O-ring 706 provides a sliding symmetric seal interface 750 between air, sometimes at low pressure, within the bore 752 of the cylinder, and a liquid medication on the opposite side of the O-ring 706.

The bore 752 of the seal cylinder 714 is provided with an internal location lip 754 at the first end which provides an inner circumferential surface 756 that abuts the drive piston stem 324 in sliding engagement. Adjacent this lip 754, between the first and second cylinder ends 716, 718, the bore 752 is provided with an internal land 758 that retains the first internal O-ring 704 of the intermediate assembly 700 via its external diameter 760. The land urges the internal diameter 762 of the O-ring 704 against the drive piston stem 324 to create a fourth sealing interface 764. The O-ring 704 provides a symmetric sliding seal, and does not function as a valve. In the present embodiment, both the first and second O-rings 704, 706 are manufactured from nitrile.

Adjacent the land 758, the cylinder bore 752 tapers outwards, to a further internal annular lip 766, also called the master piston retaining lip 766, located at the second end 718. The lip 756 couples the seal 702 to the master piston 708 as set forth below.

The intermediate vacuum seal 702 is formed as a single component from low density polyethylene, preferably by injection moulding.

Figure 12:
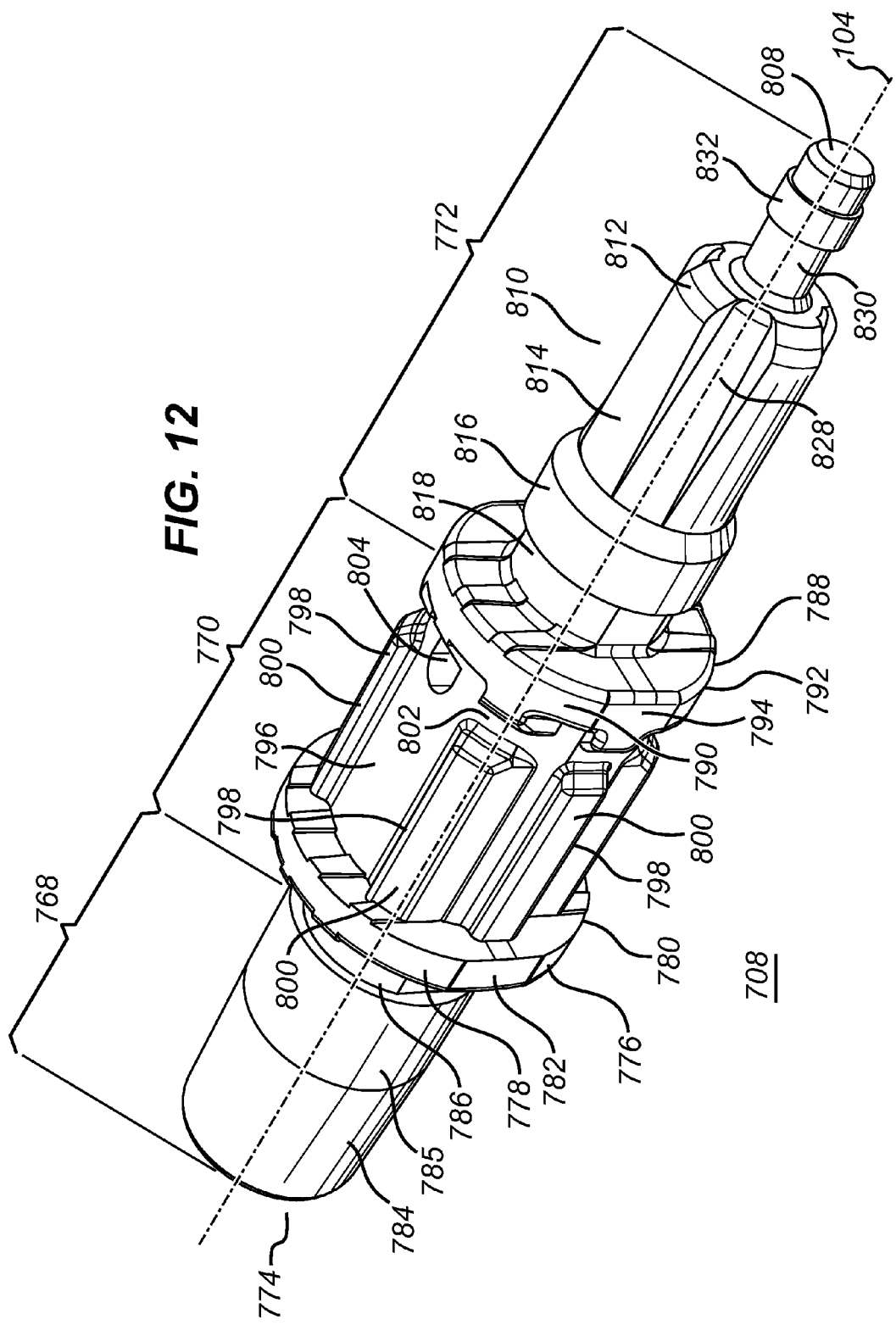
FIG. 12 shows a perspective view of a piston for use in device of FIG. 1.

With reference also to FIG. 12, which shows a perspective view of just the master piston 708 of the intermediate assembly 700, the master piston 708 comprises an elongate body which is, in large part, axisymmetric about the longitudinal device axis 104. The piston 708 can be said to comprise three sections 768, 770, 772 arranged in series;

The first section 768, also known as the retained section 768 is tubular and extends from the first end 774 of the master piston 708 to a first flange 776 which provides a first arcuate bearing surface 778 and second arcuate bearing surface 780 that abuts the internal surface of the minor vacuum bore 146. The first and second arcuate bearing surfaces 778, 780 are part of a circumference that is interrupted by a first and second chordal surface 782 (only one of which is visible in FIG. 12).

The outer surface 784 of the retained section 768 tapers outwards, from the open end 774 to a cylindrical subsection 785 which lies between the tapered part and the first flange 776. The retained section 768 and is wholly located within the intermediate vacuum seal 702, and the cylindrical subsection 785 ensures a good location with the cylinder bore 752 of the seal 702. An annular groove 786, set into the outer surface the cylindrical subsection 785 next to the flange 776, receives the master piston retaining lip 766 of the intermediate vacuum seal 702 to axially secure the piston 708 relative to the seal 702. This ensures that the seal 702 and piston 708 are coupled to one another and move axially as one component.

The second section 770, also referred to as the transfer section 770, lays within the housing actuation bore 148 in the rest state of the device 100. The section 770 extends from the first flange 776 to a second flange 788 which provides a first arcuate bearing surface 790 and second arcuate bearing surface 792 that abut the internal surface of the actuation bore 148. The first and second arcuate bearing surfaces 790, 792 are part of a circumference that is interrupted by a first and second chordal surface 794 (only one of which is visible in FIG. 12).

The outer surface 796 of the transfer section 770 is provided with a series of axial runners 798 which extend between the first and second flanges 776, 788. The runners 798 each provide an axial bearing surface 800 which engages the internal surface of the actuation bore 148. At a point towards the second flange 788, each runner 798 is relieved so that a transfer channel 802 is defined about the body of the master piston 708. The channel 802 is fed by a first and second transfer hole 804, 806, located at the top and bottom of the piston 708 (shown more clearly at FIG. 11). The holes 804, 806 are approximately aligned with the transfer conduit 196 provide to the actuation bore wall 182 as shown, however, in reality, the holes 804, 806 can be rotated about the longitudinal device axis 104, relative to the transfer conduit 196. The provision of first and second opposed holes 804, 806 ensures that a this angle has a maximum value of 90° to ensure that a good flow path is always provided between the transfer holes 804, 806 and the transfer conduit 196.

The third section 772, also referred to as the pumping section 772, extends from the second flange 788 to the second closed end 808 of the master piston 708. The pumping section 772 is a stepped piston which provides an actuation piston, via the actuation pump seal 710, and a dosing piston, via the dosing pump seal 712, on the same body.

In more detail, the pumping section 772 comprises an actuation cylinder 810, which extends from the second flange 788 to a shoulder 812 located intermediate the flange 788 and the closed piston end 808. The outer surface 814 of the actuation cylinder 810 is adapted to slidably engage the internal surface of the dosing bore 150. An external land 816 is provided to the outer surface, axially spaced from the second flange 788 to define an actuation seal retaining groove 818.

Referring to FIG. 11, the actuation pump seal 710 is an annular lip seal, comprising a locating ring 820 and a lip seal 822. The locating ring 820 is retained by the groove 818 of the pumping section 772. The lip seal 822 is located at the outer diameter of the locating ring and projects towards the second piston end 808, and radially outwards to define a conical sealing surface 824 that is of greater diameter than the actuation bore 148 in the unassembled state. The conical sealing surface 824 is pressed inwards upon assembly of the master piston 708 into the stepped bore 124 so that at least a part of the sealing surface engages the actuation bore 148 to provide a liquid tight seal interface 826 between master piston 708 and the bore 148. The tapered entry 186 to the actuation bore 148 ensures that the seal 710 is compressed gradually upon assembly of the device 100 to avoid damaging the seal.

Because of the conical geometry of the lip 822, the seal 710 acts as a one way valve, allowing some leakage past the sealing interface 826 away from the transfer section, but not in the opposite direction towards the transfer section.

The actuation pump seal 710 is formed as a single component from low density polyethylene, preferably by injection moulding.

Referring back to FIG. 12, the outer surface 814 of the actuation portion is provided with four axial flutes 828, downstream of the land 816, which extend through the shoulder 812 at the end of the actuation cylinder 810.

A dosing seal boss 830 extends from the shouldered end 812 of the actuation cylinder 810, coaxial with the actuation cylinder 810. The boss 830 is of smaller diameter than the actuation cylinder 810 and is provided with an upstanding location ring about 832 its midsection to secure the dosing pump seal 712 to the boss 830.

With reference to FIG. 11, the dosing pump seal 712 is an annular, two-way lip seal comprising a central cap 834 which fits over the boss 830. The cap 834 is defined by an annular cap wall 836 and an end wall 838, which sits at the second piston end 808.

An internal groove 840, formed in the internal surface of the annular wall 836, receives the upstanding boss ring 832. A flange 842 projects radially from the midsection of the cap 834 and is provided, at its outermost circumference, with a pair of annular lip seals, 844, 846. The first lip seal 844 projects towards the shoulder 812 of the master piston 708 and the second lip seal 846 projects away from the shoulder 812. Both lip seals 844, 846 also project radially to provide back-to-back conic sealing surfaces 848, 850 of greater diameter than the swept portion 204 of the dosing bore 150 when unassembled. Each sealing surface 848,850 is pressed inwards upon assembly of the master piston 708 into the stepped bore 124 so that at least a part of each lip seal 844, 846 provides sealing interface 852, 854 between the dosing bore 150 and the master piston 708. The tapered entry 194 to the dosing bore 150 ensures that the seal 712 is compressed gradually upon assembly of the device 100 to avoid damaging the seal 712.

The sealing interfaces 852, 854 are each one way type seals, however, their back-to-back configuration ensures that the total sealing effect of the seal 712 is symmetric i.e. leakage past the seal is prevented in both directions.

The dosing pump seal 712 is formed as a single component from low density polyethylene, preferably by injection moulding.

The master piston 708 defines blind axial bore 856 which extends from the first end 774 of the piston to a tapered end within the pumping section 772. The bore 856 is sized to receive, within the retained section 768, the stem 324 of the drive piston 302. This ensures that the contents of the bulk reservoir 336 are in flow communication, via the transfer holes 804, 806, with the external transfer channel 802 of the piston 308.

The master piston 708 is formed as a single component from polypropylene, preferably by injection moulding.

Nozzle Assembly

Figure 13:
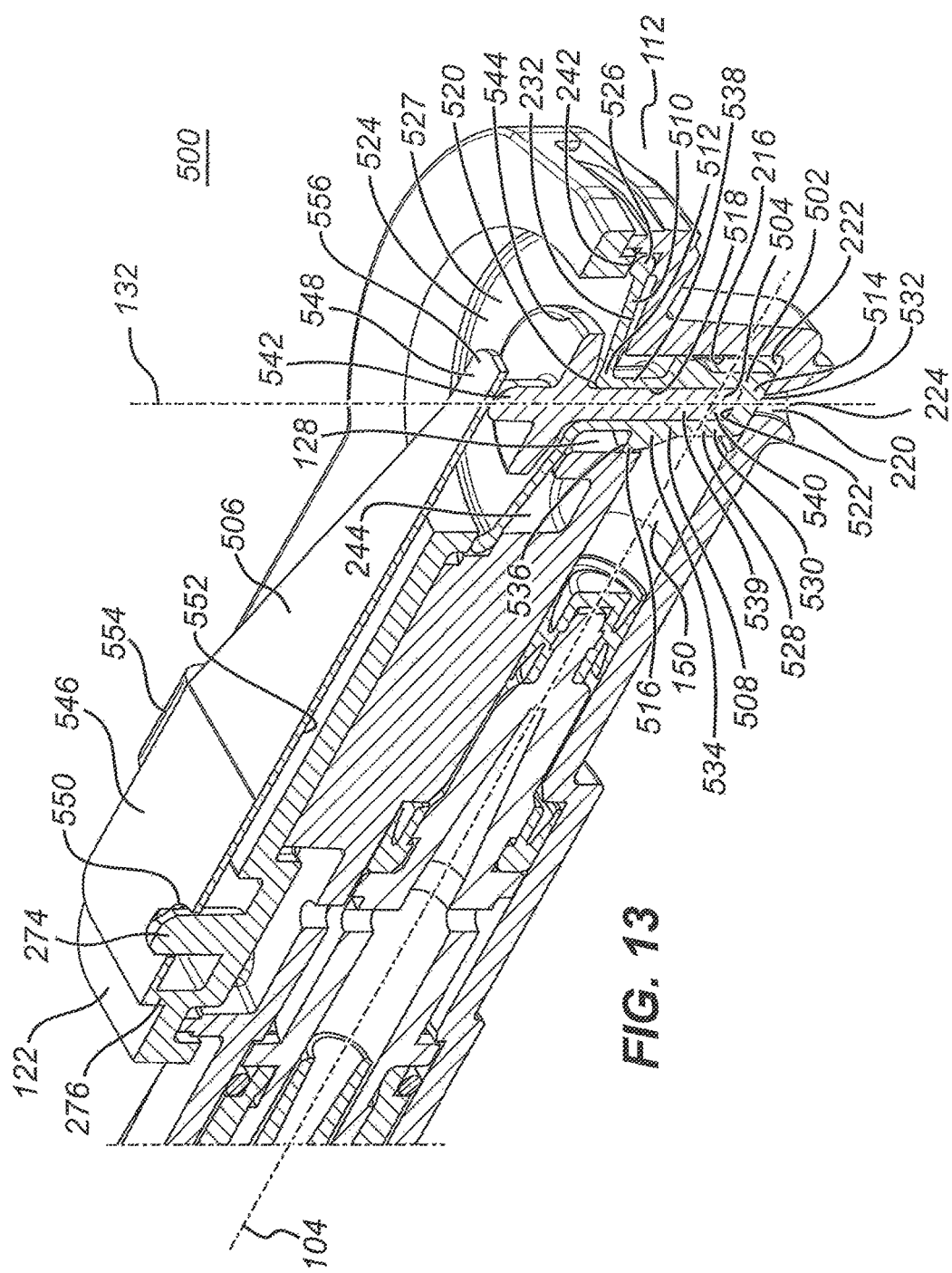
FIG. 13 shows a section through a second end of the assembled device.

Turning now to FIG. 13, the second end of the device 100 is shown in more detail in order to show the nozzle assembly 500 of the device.

The nozzle assembly 500 comprises the tip seal 502 and tip seal piston 504, slidably located within the vertical through bore 128 at the second end 112 of the device 100, and the leaf spring 506, mounted to the housing lid 122 to bear upon the tip seal piston 504.

The tip seal 502 comprises a compliant tubular body 508 provided with an actuating diaphragm 510 at a top first end 512 and a planar sealing cap 514 at the bottom second end. An annular lip seal 516 extends about the external surface of the body at a point approximately midway between the diaphragm 510 and the planar sealing cap 514 so that it seals the through bore 128 at a point above the junction with the stepped bore 124. The lip seal 516 is sized to provide a sliding liquid-tight seal between the seal 502 and the internal surface 216 of the through bore 128.

A blind socket 518 extends from an open end 520, at the centre of the diaphragm 510, to a closed end 522 formed by the sealing cap 514. The tip seal piston 504 is secured within this blind socket 518.

The actuating diaphragm 510 comprises a shallow, funnel-shaped disk 524 of substantially constant thickness which extends outwards from the tubular body 508 of the seal 502. An integral sealing bead 526 of approximately circular cross section is provided about the outer diameter of the diaphragm 510. In the assembled state, the sealing bead 526 is clamped in, and compressed by, the annular groove 242, defined between the housing main body 120 and the housing lid 122. The clamping engagement of the tip seal 502 within the housing 116 provides a microbial barrier. The upper surface 527 of the diaphragm 510 provides an external surface of the device 100 which separates the external environment from the liquid medication. The clamped assembly of the diaphragm 510 and housing 116 ensures the join between them prevents the ingress of contaminants as well as the egress of medication i.e. leakage.

The tubular body 508 comprises an annular wall 528 that extends along and about the vertical axis 132 of the through bore 128. The wall 528 comprises a cylindrical base portion 530 which extends from an external planar sealing surface 532 of the cap 514 at the bottom end of the seal 502 to a truncated bi-conic buttress 534 which tapers outwards. The lip seal 516 extends from the top, outermost edge of this support to a diameter which is slightly larger than the diameter of the through bore 128 in the unassembled state. The outer edge of the lip seal 516 is compressed inwards and upwards, i.e. towards the diaphragm, upon insertion of the tip seal 502 into the through bore 128 via the upper bore 230.

Due to the geometry of the radial lip seal 516, fluid is able to leak past it from the region below the lip 516, i.e. in the direction from the sealing face 222 toward the diaphragm 510, but not in the reverse direction. As a consequence, the lip seal 516 is able to maintain a greater pressure imbalance in a first direction i.e. with high pressure fluid above the seal and low pressure below it, than in the opposite direction, i.e. with high pressure fluid below the seal and high pressure above it.

The lip seal 516 defines an upper planar sealing face 536 which extends to a neck portion 538 of the annular wall 528 that extends from the lip seal 516 to the diaphragm 510. The neck portion 538 of the annular wall is of a reduced outer diameter than the base 530.

The tip seal 502 is made as a single piece from EPDM rubber in the present embodiment.

The tip seal piston 504 comprises an elongate rod 539 which extends from its base 540, located at the closed end 522 of the tip seal socket 518, to a free end 542 which stand proud of the upper surface 266 of the housing lid 122 when the seal assembly 500 is assembled. A circular flange 544 extends about the rod 539 a point between the upper free end 542 and the upper diaphragm surface 527. In the rest state the flange 544 is spaced apart from the diaphragm 510.

The upper free end 542 of the tip seal piston 504 is domed.

The tip seal piston 504 is formed from polypropylene in the present embodiment. Preferably the tip seal 502 and tip seal piston 504 are each injection moulded. Still more preferably, the tip seal 502 and tip seal piston 504 are injection moulded in the same mould tool via two-shot injection moulding process.

The leaf spring 506 comprises a resilient stainless steel plate which extends from a mounted end 546, to a free, bearing end 548. At the mounted end 546, the spring defines a mounting hole 550 that fits over the upstanding peg 274 of the housing lid 122. The lower surface of the spring 506 rests upon the walls 276, 278, 280 which space it apart from the upper surface of the housing lid 122. Only the traverse wall 276 is visible in FIG. 13.

A pair of arms 554 (only one visible) extend laterally from the mounted end 546 of the spring 506 and wrap around the housing lid 122, passing through flange cut-outs 262 on either side of the main body 120 to clamp the exposed under surface of the lid 122. This ensures that the spring 506 is firmly clamped to the housing lid 122 to ensure consistency of operation.

The free end 548 of the spring 506 extends from the mounted section to a point above the tip seal piston 504. The spring 506 end tapers inwards from the mounted end 546 to define an elongate tip 556 which abuts the domed head of the tip seal piston 504.

In the rest state show, the leaf spring 506 positively engages the domed head 542 of the piston 504 to urge it downwards along the vertical axis 132 of the bore 128. The domed head 542 and the length of the free end of the leaf spring are chosen to ensure that the force applied by the underside 552 of the spring 506, to the tip seal is closely aligned with the vertical bore axis 132, minimising rocking of the tip seal piston 504 and tip seal 502 within the bore 128.

The lower end of the piston 504 drives the closed base of the tip seal 502 against the sealing face 222 at the base of the through bore to seal the outlet orifice 220. Furthermore, the spring force applied by the leaf spring 506 to the tip seal 502 via the tip seal piston 504 is sufficient to ensure the tip seal 502 is compressed beyond the nominal point at which it seals the outlet orifice 220.

In the present embodiment, the spring 506 applies a load of about 7.5 N to the free end 542 of the tip seal piston 504 to bias the tip seal 502 against the housing sealing face 222. This results in a clamping force between the external sealing surface 532 of the piston seal, and the sealing face 222 within the through bore 128 of about 5 N. This is in excess of the 3 N required to seal the sealing interface formed between the two which has an area of approximately 3.75 mm².

Variable Volume Chambers

Figure 14:
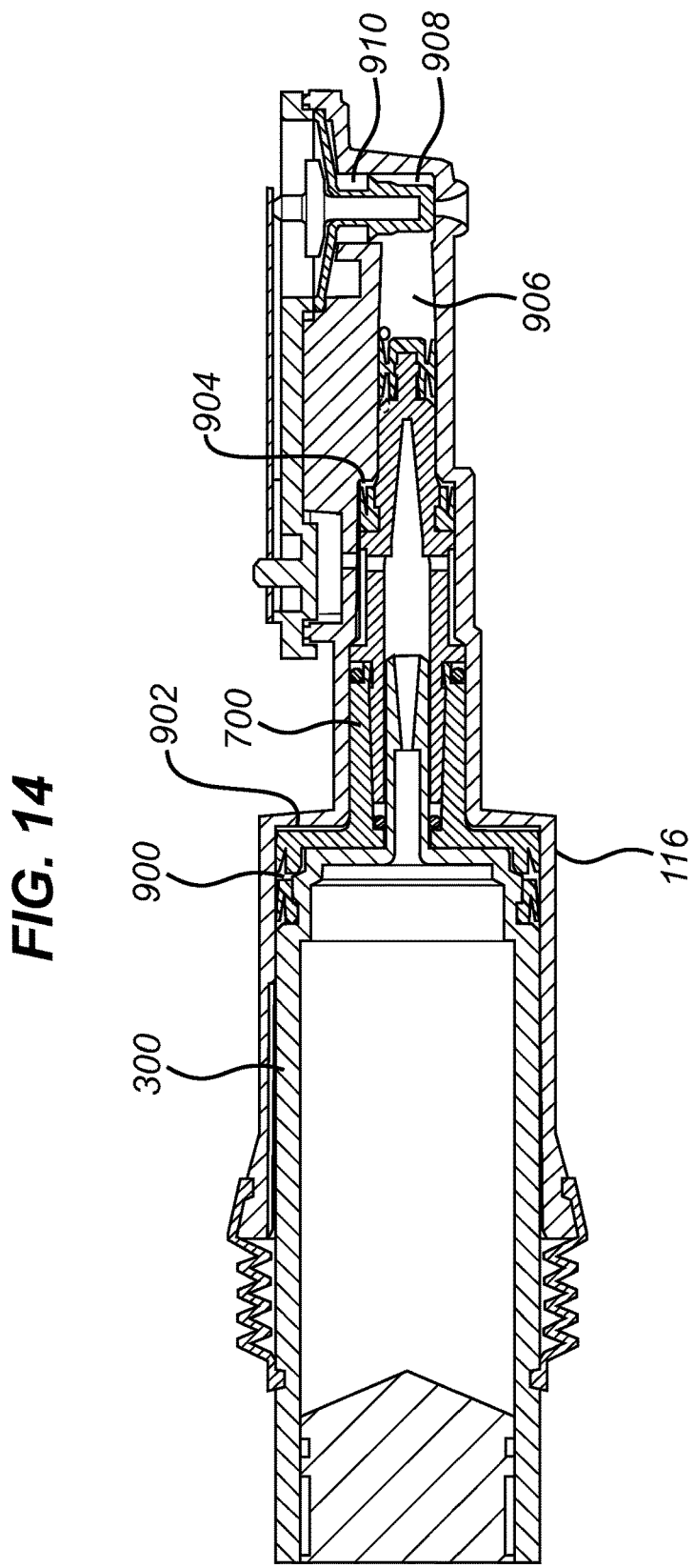
FIG. 14 shows a section through the device as per FIG. 3.

As assembled, the device 100 defines a plurality of variable volume chambers which are key to the operation of the dispenser 100. Turning to FIG. 14 there is shown a section through the device as per FIG. 3.

First Vacuum Chamber

A coupling vacuum chamber 900 is defined between the device housing 116, the reservoir assembly 300 and the intermediate assembly 700.

In more detail, and with reference also to FIG. 11, the chamber 900 is defined between the internal surface 152 of the major vacuum bore 162, the reservoir vacuum seal 306, reservoir bulkhead 314 and reservoir stem 324, and by the intermediate vacuum seal 702, particularly the lip seal 734, second disk face 726, and first O-ring 704.

The vacuum chamber 900 is shown in a contracted state, with the device 100 at rest. It can be seen that, in this rest state, the sealing disk 720 of the intermediate vacuum seal 702 is adapted to conform closely to the bulkhead 314 of the reservoir assembly 300. This minimises the volume of the coupling vacuum chamber 900 in the contracted state, minimising the volume of ambient air held by the chamber. This improves the effectiveness of the chamber 900 in operation, as described below.

The vacuum chamber 900 is slidably moveable from this rest position by movement of the drive piston 302 and intermediate assembly 700. The integrity of the chamber 900 is maintained by the first sealing interface 352, provided between the reservoir vacuum seal 306 and the major vacuum bore 162, and by the second sealing interface 740, provided between the intermediate seal 702 and the major vacuum bore 162.

Second Vacuum Chamber

An actuation vacuum chamber 902 is defined between the device housing 116 and the intermediate assembly 700.

In more detail, and with reference also to FIG. 11, the chamber 902 is defined by the internal surface 152 of the major vacuum bore 162, the internal surface of the distal wall 156, the internal surface of the minor vacuum bore wall 146, and by the intermediate vacuum seal 702, particularly the lip seal 734, first disk face 724, the vacuum seal outer surface 742 and the second O-ring 706.

The actuation vacuum chamber 902 is shown in a contracted state, with the device 100 at rest. In this rest state, the sealing disk 720 and outer surface 742 of the intermediate vacuum seal 702 are adapted to conform closely to the distal bore end 158, and the internal surface of the minor vacuum bore 146. This minimises the volume of ambient air held by the chamber to improve the effectiveness of the chamber 900 in operation, as described below.

The chamber 902 is expandable from the contracted state shown by sliding the actuation vacuum seal towards the open end of the drive bore 144.

The integrity of the actuation vacuum chamber is maintained by the second sealing interface, generated between the lip seal 734 and the internal surface 152 of the major vacuum bore 162, and by the third sealing interface 750, provided between the second O-ring and the internal surface of the minor vacuum bore 146.

With reference to FIG. 11, the coupling vacuum chamber 900 has a greater swept area than the actuation vacuum chamber 902 as the area of the piston bulkhead 314 and sealing disk second face 726 is larger than the area of the sealing disk first face 724 and first bore end wall 156 outboard of the intermediate seal outer surface 742.

The greater swept area of the coupling vacuum chamber 900 ensures that, for a given expansion along the device axis 104, the increase in volume of the first chamber 900 is greater than the increase in volume of the actuation vacuum chamber 902. This ensures that, as the master piston 708 is withdrawn from the housing 116, the actuation vacuum chamber 902 expands in preference to the coupling vacuum chamber 900. As such, the coupling vacuum chamber 900 locks the intermediate assembly 700 to the drive piston during the energizing steps of the device cycle, shown at FIG. 16A through FIG. 18B.

Actuation Pump

An actuation pump 904, comprising a variable volume chamber 904, is defined between the housing 116 and the intermediate assembly 700, as can be seen with reference to FIG. 14.

In more detail, and with reference also to FIG. 11 and FIG. 12, the actuation pump 904 is defined by the internal surface of the actuation bore 148, the internal surface of the dosing bore 150, and by the external surface of the master piston 708 between the actuation pump seal 710, and the dosing pump seal 712, as well as the seals 710, 712 themselves.

FIG. 14 shows the actuation pump 904 in a rest position in a contracted state. The chamber 904 is expandable from this contracted state by sliding the intermediate assembly 700 towards the open end of the drive bore.

Dosing Pump

A dosing pump 906, comprising a variable volume chamber 906, is defined between the housing 116, the intermediate assembly 700 and the nozzle assembly 500, including the tip seal 502. The dosing pump 906 is adapted to deliver a metered dose of a liquid medication as detailed below.

In more detail, and with reference also to FIG. 13, the dosing pump 906 is defined between the dosing pump seal 712, the internal surface of the dosing bore 150, the internal surface 216 of the through bore 128, the sealing face 222 and the cylindrical base 530 and lip seal 516 of the tip seal 502. In particular, it can be see that the tip seal 502 cooperates with through bore 128 to define an annular dosing pump 908 between the sealing face 222 and lip seal 516, which is in flow communication with the dosing bore 150 of the stepped bore 124.

FIG. 14 shows the dosing pump 906 in a rest position in a contracted state. The chamber 904 is expandable from this contracted state by sliding the intermediate assembly 700 towards the open end of the drive bore.

Tip Seal Actuation Chamber

A tip seal actuation chamber 910 is defined between the housing 116 and the nozzle assembly 500.

In more detail, and with reference also to FIG. 13, the chamber 910 is defined between the lip seal 516 and the lower face of the actuation diaphragm 510, by the wall of the through bore 128 between the lip seal 516 and diaphragm 510, by the shallow conical base 232 of the through bore 128 and also by the recess 244.

Operation of Device

FIGS. 15-21 show, schematically, the device operation cycle.

Turning to FIG. 15A through 15C, the device 100 is will now be described at rest. FIG. 15A shows a first section through the device 100 at rest, showing the second reservoir 199, and a part of the first reservoir 197, and FIG. 15B shows a second section through the device 100 at rest, showing the first reservoir 197 and the plenum chamber 211. FIG. 15C shows a flow diagram of the device 100 at rest.

In the rest state, the drive piston 302 abuts the intermediate assembly 700 which in turn abuts the drive bore distal wall 156. As a consequence, the coupling vacuum chamber 900 and actuation vacuum chamber 902 are both in their contracted state and have minimal volume. Both chambers 900, 902 are filled with air at ambient pressure.

The first reservoir 197 is in permanent fluid communication with the bulk reservoir 336 via the transfer conduit 196, transfer ports 804, (also 806, not shown), the reservoir lumen 330, and master piston bore 856. Notably, the bypass flute 198 provided to the actuation bore ensures that the first reservoir 197 is in flow communication with the bulk reservoir 336 throughout the operation cycle, irrespective of the position of the actuation pump seal 710. In particular, the flute 198 bypasses the seal 710 when the seal 710 lies on the bulk reservoir 336 side of the transfer conduit 196 and would otherwise isolate the first reservoir 197 from the bulk reservoir 336.

At rest, the actuation pump seal 710 lies adjacent the actuation bore distal end 188, so that the actuation pump 904 is in its contracted state. The chamber 710 is filled with liquid medication 912.

The actuation pump 904 is in flow communication with the first reservoir 197 via the control conduit 208, between the chamber 904 and the first reservoir 197. The chamber is also in fluid communication with the second reservoir 199 via the actuation conduit 202 which is not sealed by the actuation pump seal 710 in the rest state.

The tip seal actuation chamber 910 is in flow communication with the second reservoir 199 via the horizontal conduit 246, and remains so throughout the operation cycle of the device 100. At rest, the tip seal actuation chamber 910 is filled with medication 912, at ambient pressure.

Hence, at rest, the bulk reservoir 336 is in flow communication with the first reservoir 197, and also with the actuation pump 904, the second reservoir 199, and the tip seal actuation chamber 910. This ensures that pressure in the liquid medication 912 throughout these regions is able to substantially equalize, via movement of the reservoir plug 304, with the ambient pressure external to the device 100. This ensures that pressures within the device 100 are not substantially above atmospheric, which could lead to leakages, or "jetting" upon dosing. Similarly, it ensures that pressures within the device 100 do not fall substantially below atmospheric, which could draw external contaminants into the device 100.

In the rest state, the dosing pump 906 and plenum chamber 211 are together isolated from the rest of the device 100 as a closed metering system 914, shown schematically at FIG. 15C. The dosing pump seal 712 lies at the distal end of the cylindrical subsection 204 to place the chamber 906 in its contracted state. The seal 712 closes the control conduit 208, and thereby isolates the chamber 906, and plenum, from the first reservoir 197. The chamber 906 is also isolated from the external environment by the tip seal 502, which is closed against the outlet orifice 220 by the leaf spring 506.

At rest, the chamber 906 is filled with medication 912 which is at above external ambient pressure, slightly pressurised by the action of the tip seal lip seal 516, which is pushed into the chamber under the force of the leaf spring 506.

The plenum 211 is in permanent flow communication with the dosing pump 906 via the plenum conduit 210. The plenum is deliberately filled with air, and this air is pressure balanced to the same pressure as the medication 912 in the dosing pump 906 via the plenum conduit 210. It will be appreciated that where the medication is susceptible to degradation via contact with air, e.g. via oxidation, the plenum 211 could instead be filled with an inert gas, such as nitrogen.

The radial lip seal 516 provided about the tip seal is able to deform, to allow liquid 912 from the dosing pump 906 into the tip seal actuation chamber 910 in the event that the pressure difference is great enough i.e. the pressure in the dosing pump 906 sufficiently exceeds that in the tip seal actuation chamber 910. As set forth previously, the tip seal actuation chamber 910 is in flow communication with the bulk reservoir 336 at rest, and therefore able to accommodate such leakage, which therefore serves to pressure relieve the dosing pump 906 as necessary. Hence, by using the same liquid medication 912 for the actuation pump 904 as delivered by the dosing pump 906, it is possible to allow some leakage past the lip seal 516 to accommodate pressure spikes in the dosing chamber 906. Also, the use of a common liquid to both pumps 904, 906, eliminates the possibility of contamination of the liquid medication by a separate working liquid for the actuation pump 904, were a separate working liquid to be used.

The sealed gas reservoir 372 within the bellows contains air at ambient pressure.

User Operation—Actuator

With reference to FIG. 3, the drive piston 302, intermediate vacuum seal 702 and housing 116 provide an actuator for operating the device 100.

In more detail, to operate the device 100, a user pulls a pair of opposed reservoir actuation lugs 916, which protrude externally from near the open end of the drive piston 302 (as shown at FIG. 2), away from a pair of opposed housing lugs 918 (only one shown at FIG. 2), which protrude externally from adjacent the end wall 156 of the drive bore 144.

In this way, the user energizes the device 100 for delivery of liquid medication by drawing the drive piston 302 out of the housing 116 to an energized position as shown in FIG. 18A and FIG. 18B.

In the position shown at FIG. 18*a*, 18*b*, the drive piston/reservoir vacuum seal 306 lies next to, but not over, the axial inlet flutes 170. Up to this stage of operation, movement of the drive piston 302 causes movement of the intermediate vacuum seal 702, and thus operation of the attached actuation pump 904 and dosing pump 906. The drive piston 302 is couple to the intermediate vacuum seal 702 by operation of the coupling vacuum chamber 900 which is sealed and so resists expansion.

Hence withdrawal of the drive piston 302 also withdraws the intermediate vacuum seal 702 from the housing which expands the actuation vacuum chamber 902, in effect, storing actuation energy (although the energy is in reality stored external to the vacuum chamber 902 by air displaced by the withdrawal of the drive piston 302).

Once the drive piston 302 is pulled beyond the flutes 170 in the housing, as shown in at FIGS. 19a and 19b, the coupling vacuum chamber 900 is unsealed, releasing the intermediate vacuum seal 702 from the drive piston 302. Hence, from this stage of the operation cycle, the intermediate vacuum seal 702 moves independently of the drive piston 302 and thus independently of user input to the dispenser 100.

Moreover, the movement of the intermediate assembly 700 is now driven by the pressure of atmospheric air entering the coupling vacuum chamber 900. The low pressure maintained by the actuation vacuum chamber 902 creates a pressure differential across the sealing disk 720 of the intermediate assembly 700 which drives the intermediate assembly 700 back into the device. This in turn powers the delivery phases of the device as set out in more detail below.

Operation Cycle of Dispenser
First Stage—Priming Phase 1

Turning now to FIG. 16A through FIG. 16C, there are shown the same views as FIG. 15A through FIG. 15C but with the device 100 in a first stage of operation. In this first stage of operation, the drive piston 302 is withdrawn from the housing 116 by pulling the reservoir lugs 916 (FIG. 2) away from the housing lugs (918, FIG. 2). Withdrawal of the drive piston 302 in turn draws the intermediate assembly 700 away from the drive bore distal wall 156 due to the action of the coupling vacuum chamber which couples the assembly 700 to the drive piston.

As a consequence, the actuation vacuum chamber 902 is expanded, which causes pressure of air within the chamber 902 to fall below ambient. The work required to expand the actuation vacuum chamber 902 is in effect stored via the sub-ambient pressure within the chamber 902.

Movement of the intermediate assembly 700 draws master piston 708 and actuation pump seal 710 away from the actuation bore distal end 188, to expand the actuation pump 904.

The dosing pump seal 710 separates the actuation pump 904 from the control conduit 208, substantially isolating the actuation pump from the first reservoir 197, and hence from the bulk reservoir 336. This has the further effect of substantially isolating the second reservoir 199 and tip seal actuation chamber 910 from the bulk reservoir 336.

As a result, expansion of the actuation pump 904 causes a local drop in pressure in the actuation pump 904, the second reservoir 199 and the tip seal actuation chamber 910.

The actuation pump seal 710 provides a small one way flow path from the first reservoir 197 which allows some leakage under the pressure difference created by the expansion of the actuation pump 904 (the first reservoir 197 remains at ambient as it is in permanent flow communication with the bulk reservoir 336). This is indicated at FIG. 16C by broken arrow 920.

The flow 920 of medication 912 past the seal 710 reduces the drop in pressure within the actuation pump 904, thereby preventing hydraulic lock and reducing the actuation force required to withdraw the drive piston 302.

Movement of the intermediate assembly 700 also moves the dosing pump seal 712 away from the distal end of the cylindrical subsection 204, expanding the dosing pump 906. The dosing pump 906 is isolated from any source of liquid medication in the first stage of operation; hence the increase in volume causes a drop in pressure within the pump 906 as there is insufficient liquid to fill the pump.

Air within the plenum chamber 211 expands to take up the increased volume. This reduces the pressure of the plenum and dosing pump 906 to below ambient, but prevents the creation of a vacuum lock that might otherwise prevent actuation of the device 100. The tip seal 502 is also able to deform into the dosing pump 906 to reduce the rarefaction caused by expansion of the dosing pump 906.

The tip seal actuation chamber 910 remains filled with medication 912, again at ambient pressure.

Second Stage—Priming Phase 2

With reference to FIG. 17A through FIG. 17C, in a second stage of operation, also known as the dosing priming stage, the drive piston 302 is withdrawn further from the housing 116 so that the dosing pump seal 712 uncovers the control conduit 208, and moves to place the dosing pump 906 in fluid communication with the first reservoir 197 via the control conduit 208.

Because the first reservoir 197 is in permanent flow communication with the bulk reservoir 336, liquid medication flows from the first reservoir 197 into the dosing pump 906, as shown at FIG. 17C by arrow 922. This causes the dosing pump 906 to be filled with liquid medication 912 at ambient pressure. The air within the plenum chamber 211 is therefore also returned to atmospheric pressure.

The piston 302 draws the intermediate assembly 700 further away from the drive bore distal wall 156 to further expand the actuation vacuum chamber 902 so that pressure within the chamber 902 falls further below ambient.

The actuation pump 904, second reservoir 199 and tip seal actuation chamber 910 remain partially filled with liquid medication 912 at below atmospheric pressure.

Third Stage—Priming Phase 3

With reference to FIG. 18A through FIG. 18C, in a third stage of operation, also known as the actuation priming stage, the drive piston 302 is withdrawn further from the housing 116 so that the vacuum seal 306 lies next to, but not abutting, the inlet flutes 170 i.e. at the commitment annulus 164 (shown at FIG. 4).

The piston 302 draws the intermediate assembly 700 further away from the drive bore distal wall 156 to further expand the actuation vacuum chamber 902 so that pressure within the chamber 902 falls further below ambient.

Movement of the intermediate assembly 700 causes the actuation pump seal 710 to uncover the transfer conduit 196, and places the actuation pump 904 in flow communication with the first reservoir 197, with the result that liquid medication 912 flows from the first reservoir 197 to the actuation pump 904, as indicated by arrow 924. Because the first reservoir 197 is in permanent flow communication with the bulk reservoir 336, the actuation pump is filled with liquid medication 912 at ambient pressure.

In summary, at the third stage of actuation, shown at FIGS. 18A through 18C, the actuation pump 904 and dosing pump 906 are at their maximum volume and are both filled with liquid medication 912 at ambient pressure. The plenum 211 is filled with air at normal pressure, while the tip seal actuation chamber 910 is filled with liquid medication 912 at ambient pressure.

By priming, i.e. filling the expanded dosing pump 906 before priming of the expanded actuation pump 904, a possible misuse scenario is avoided wherein the tip seal 502 could be opened without pressurised liquid 912 present within the dosing pump 906.

By ensuring that the dosing pump 906 is filled before opening, and furthermore, that the dosing pump is slightly pressurised before opening of the tip seal, the device 100 ensures that air cannot enter the dosing pump 904 upon opening of the outlet orifice 220.

Fourth Stage—Activation

With reference to FIG. 19A through FIG. 19C, in a fourth stage of operation, also known as the activation phase, the drive piston 302 is withdrawn fractionally further from the housing 116, so that the vacuum seal 306 overlies the inlet flutes 170. This is the maximum distance that the piston 302 is withdrawn from the housing 116.

The inlet flutes 170 interrupt the sealing interface 352 between the coupling vacuum seal 306 and the housing 116 so that the gas reservoir 372 is placed in flow communication with the coupling vacuum chamber 900. This allows air to flow from the reservoir 372 down the flutes 170, and past the seal 306 into the chamber 900. The airflow into the chamber 900 raises the pressure within the coupling vacuum chamber 900 and releases the lock between the intermediate assembly 700 and the drive piston 302.

The increase in pressure within the coupling vacuum chamber 900 creates a pressure imbalance across the sealing disk 720 which separates the coupling vacuum 900 from the actuation vacuum 902. This causes the intermediate assembly 700 to be driven towards the drive piston bore distal end 158. The flow rate of air into the chamber 900 controls the rate at which the intermediate assembly returns to its rest position, shown in FIG. 15A and FIG. 15B.

As a consequence, the intermediate assembly 700 of the device 100 now is now powered independently of any further user effort applied to the drive piston 302 for the final stages of the actuation cycle. The location of the commitment annulus 164 therefore allows the total actuation energy to be predetermined, and guarantees that this predetermined energy will be reached and stored before its release to drive the intermediate assembly back to the rest state.

The rate of airflow into the coupling vacuum chamber 900 is throttled by the flutes 170, which gives good control of the rate of energy release into the intermediate assembly 700 and nozzle assembly 500 for dosing when compared with other energy storage systems, such as coil springs. The size and number of the flutes 170 can be chosen to define the rate of energy released to drive the intermediate assembly 700 to its resting position.

This good control of energy into the system has been found to be important for good droplet formation.

Fifth Stage—Priming Phase 4

Figure 20C:
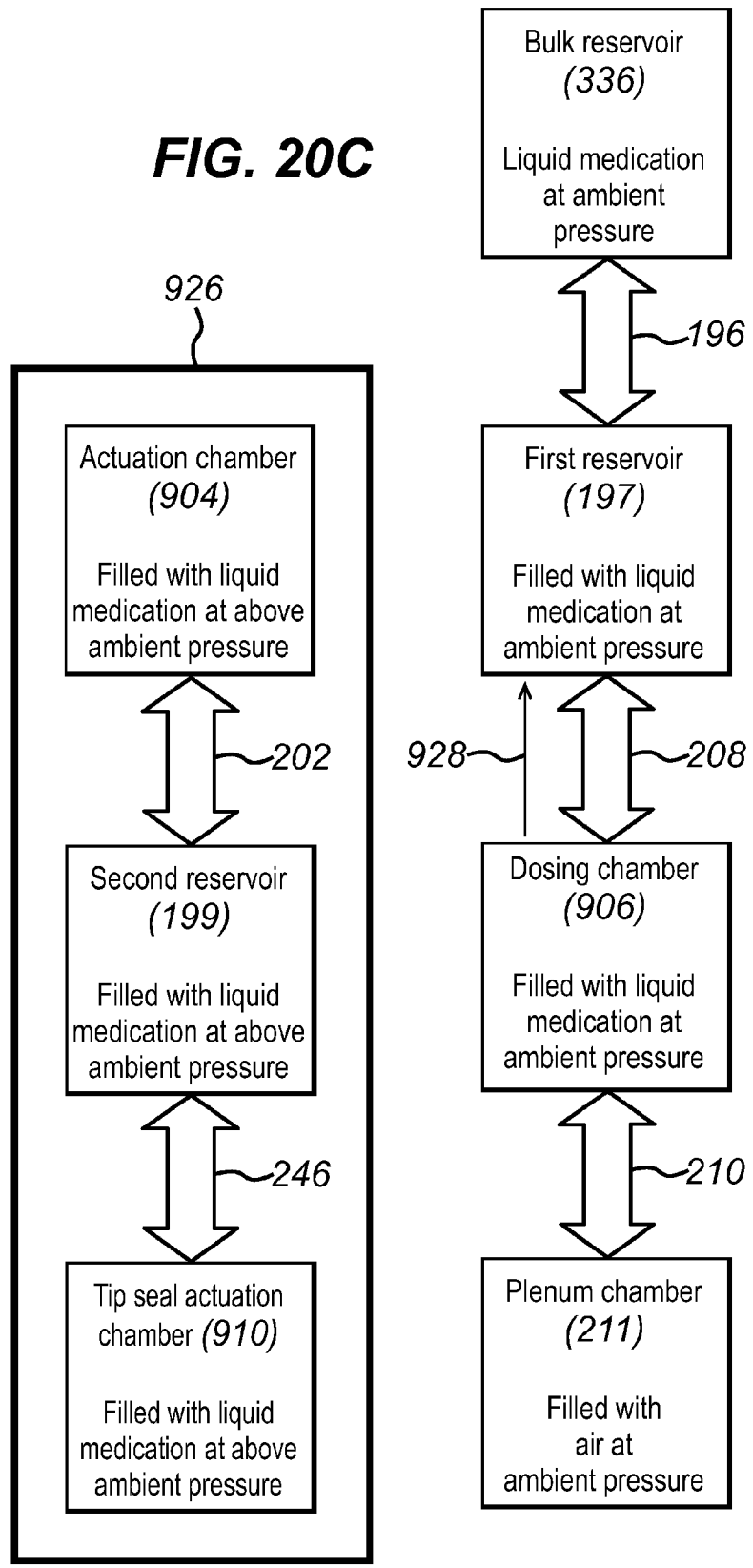

With reference to FIGS. 20A through 20C, in a fourth, bleed, stage of operation, the intermediate assembly 700 moves towards its rest state so that the actuation pump seal 710 covers the transfer conduit 196 between the actuation bore 148 and the first reservoir 197.

Once the seal 710 has passed the transfer conduit 196 in the return direction, the one way nature of the lip seal 710 ensures that fluid cannot escape the actuation pump 904. A continuous closed actuation volume 926, shown schematically at FIG. 20C, is therefore defined by the actuation pump 904, second through hole 202, second reservoir 199, horizontal conduit 246 and tip seal actuation chamber 910.

As a consequence, further movement of the intermediate assembly 700 towards the rest position reduces the volume of the actuation pump 904 which pressurises medication 912 within the closed volume 926. The resultant pressurisation of the tip seal actuation chamber 910 applies a hydraulic lifting force to the underside of the tip seal diaphragm 510.

Movement of the intermediate assembly 700 also moves the dosing pump seal 712 towards the distal end of the cylindrical subsection 204. The control conduit 208, between the dosing bore 150 and the first reservoir 197 remains uncovered, which allows medication 912 within the dosing pump 906 to be bled back to the reservoir 336. In more detail, the liquid 912 flows from the pump 906 to the first reservoir 197, via the control conduit 208, as shown schematically at FIG. 20C by arrow 928.

Sixth Stage—First Delivery Phase

With reference to FIG. 21A through FIG. 21C, in a sixth stage of operation, which initiates release of medication 912 from the device outlet orifice 220, the intermediate assembly 700 moves further towards its rest state which further pressurises the continuous closed volume 926. As a consequence, the resultant pressurisation of the tip seal actuation chamber 910 increases the hydraulic lifting force applied to the underside of the tip seal diaphragm 510 to a hydraulic opening force, which overcomes the spring force applied by the leaf spring 506 to the tip seal 502 via the tip seal piston 504.

This causes the tip seal 502, particularly the tip seal cap 514, to be decompressed, and then lifted to unseal the outlet orifice 220.

During decompression of the tip seal cap, i.e. while the orifice 220 is still sealed, movement of the master piston 708 also moves the dosing pump seal 712 towards the distal end of the cylindrical subsection 204, past the control conduit 208. This seals the dosing pump 906 so that further movement of the master piston 708 towards the rest position displaces liquid under minimal pressure out of the unsealed outlet orifice 220.

In more detail, the compression of the tip seal by the leaf spring 506 is chosen such that the tip seal cap 514 only begins to unseat from the sealing surface 222 when there is a positive pressure in the dosing pump 906.

Furthermore, as the lip seal 516 is moved upwards, away from the orifice 220, the volume of the annular chamber 908 below the seal 516 increases. This increase in volume partially offsets the reduction in volume of the dosing pump 906 cause by the movement of the dosing pump seal 712 towards the orifice 220 whilst enabling pressurisation of the liquid within the dosing pump 906. In other words, the opening of the tip seal slows the effective speed at which the dosing pump 906 contracts. This in turn ensures that medication is delivered to the outlet orifice 220 at slow speed so that a metered dose of liquid 912 is substantially retained within the pump 906 until a second phase of delivery, which is described below. This minimises leakage from the orifice 220.

The ratio of the swept area of the actuation pump 904 to the swept area of the tip seal actuation chamber 910 allows the conversion of a relatively large movement of the master piston 708 into a shorter, but more powerful movement of the tip seal diaphragm in order to overcome the spring force applied by the leaf spring 506.

During the sixth dosing stage of operation, the plenum chamber 211 absorbs any spikes in the fluid pressure within the dosing pump 906 to avoid jetting at the outlet orifice 220. Without wishing to be bound by theory, it is believed that the plenum 211 acts as a gas spring, which absorbs spikes in energy through the dosing stage of operation.

Seventh Stage—Second Delivery Phase

With reference to FIG. 22A through FIG. 22C, in a seventh stage of operation, which terminates release of medication 912 from the device outlet orifice 220, the intermediate assembly 700 moves further towards its rest state, so that the dosing pump seal 712 passes beyond the control conduit 208 between the dosing bore 150 and the first reservoir 197. Thereby isolating the dosing pump 906 from the first reservoir 197, and venting the actuation pump 904 to atmospheric pressure by placing it in fluid communication with the first reservoir 197.

This opens and vents the continuous closed actuation volume 926 formed during stages five and six of operation. In more detail, and with reference to FIG. 22C, pressurised liquid in the second reservoir 199 can now flow into the actuation pump 904, via the actuation conduit 202 and via the shoulder of the master piston 708 (shown at FIG. 12) through the control conduit 208 into the first reservoir 197. This relief flow is shown schematically by 930

The venting of the continuous closed actuation volume 926 removes the upward force on the tip seal diaphragm 510. This allows the leaf spring 506 to force the tip seal 502 into sealing engagement with the sealing surface 222 to seal the outlet orifice.

The motion of the tip seal 502 towards the outlet orifice 220 now reduces the volume of the annular chamber 908, which in combination with the continued motion of the dosing pump seal 712, increases the speed at which the dosing pump 906 contracts when compared with the first delivery phase, described above. This increases the speed at which the medication 912 is delivered to the outlet orifice and therefore sweeps the metered dose of medication out of the dosing pump 906, dispensing a droplet 930 of medication from the orifice 220.

The master piston 708 is configured such that the dosing pump seal 712 continues to move after the tip seal 502 has closed the outlet orifice 220. This ensures that liquid flows out of the orifice until it is sealed close to prevent ingress of contaminants. The remaining movement is minimised so that the contents of the dosing pump 906 are only slightly pressurised, along with the air in the plenum chamber 211.

The metered volume dose of the dispensed droplet 930 is defined by the volume swept by the dosing pump seal 712 between the point at which it seals the dosing pump 906 from the first reservoir 197 (start of first delivery phase), to the point at which the same seal 712 vents the actuation circuit 926, by uncovering the control conduit 208 (start of second delivery phase).

Hence, the metered dose is controlled only by the geometry of the dosing pump seal 712, the geometry of the hole, and the geometry of the dosing bore 150. This enables good manufacturing control of the metered dose.

In order to deliver a droplet of medication, it is desirable to deliver the metered dose with low hydraulic energy, preferably between 0.03252 mJ/s and 0.120 mJ/s. To this end, it is preferred that the dosing pump 906 is pressurised to between 0.002 bar and 0.095 bar at dosing i.e. during opening of the outlet orifice 220. To ensure that the sealing force applied between the tip seal 502 and the sealing face 222, is overcome in a reliable and consistent way, it is preferred that the actuation circuit provides an actuation pressure of about 1.77 bar at dosing.

Eighth Stage—Purge Phase

In a final stage of the dispensing cycle, the intermediate assembly 700 returns to the rest state set forth with reference to FIGS. 1 through 15C above. The drive piston 302 is then returned home by the user, or by some actuator operated by the user, which urges the reservoir actuation lugs 916 towards the housing actuation lugs.

As the drive piston 302 is pushed home, the one way vacuum seal 306 allows air to be expelled from the coupling vacuum chamber 900 back into the sealed gas reservoir 372. This ensures that the chamber 900 contains a minimal volume of air at ambient pressure when in the rest state shown in FIGS. 15A and 15B.

The use of the gas reservoir 372 to isolate the air cycled into, and out of, the coupling vacuum chamber 900 from the external environment helps to prevent contaminants from entering the coupling vacuum chamber and potential further ingress into the medication 912 within the device 100.

Furthermore, as the drive piston 302 is pushed against the intermediate assembly sealing disk 720, the disk 720 is positively located against the reservoir bore distal end 158. The one way lip seal 734 allows any air that has entered the actuation vacuum chamber 902 to be expelled past the seal as it is seated home. This again ensures that the actuation vacuum chamber contains a minimal volume of air at ambient pressure when in the rest state of the device 100.

The above described device has been designed to dispense a droplet of 40 μl. However, with modification, the device has been able to meter a dose as small as 4.53 μl of water in testing. For such small doses, it has been found advantageous to replace the lip seal, used to provide the dosing pump seal 712, with an O-ring seal.

Data for 30 actuations with water was collected for a device adapted with such an O-ring seal in place of the lip seal; The mean drop weight was measured at 5.63 μl and the minimum drop weight was measured at 4.53 μl.

The maximum drop weight was measured at 7.19 μl. The range of the 30 actuations was +/−30% of the mean.

For 28 out of 30 actuations a pendant drop was formed and remained on the exit nozzle. The data indicates that the PFMD Pump Technology would be able to reliably meter 10 μl drops.

What is claimed is:

1. A dispenser for the delivery of a droplet of a liquid, comprising a housing which defines an outlet orifice, a tip seal, biased against the housing to seal the outlet orifice, and a dosing pump for pumping a liquid to an outlet nozzle, wherein the dispenser further comprises an actuation pump configured to provide a hydraulic opening force to the tip seal for opening of the outlet orifice, wherein the actuation pump is configured to operate at a higher hydraulic pressure than the dosing pump.

2. A dispenser as claimed in claim 1 configured such that the operation of the dispenser causes the dosing pump to be primed before the actuation pump is primed.

3. A dispenser as claimed in claim 1 wherein the dosing pump and actuation pump are defined by at least one common component comprising a stepped piston.

4. A dispenser as claimed in claim 1 configured such that, in use, delivery of the droplet comprises a first phase during which the dosing pump contracts at a first speed, and a second phase during which the dosing pump contracts at a second, higher speed.

5. A dispenser as claimed in claim 4 wherein the dosing pump is partly defined by the tip seal such that operation of the tip seal causes the different effective speeds in contraction of the dosing pump during the first and second phase of opening.

6. A dispenser as claimed in claim 1 wherein the actuation pump and dosing pump use a common liquid.

7. A dispenser as claimed in claim 1 wherein the actuation pump is in part defined between a first seal and a second seal, and wherein the actuation pump is configured such that motion of at least one first or second seal controls liquid flow into the actuation pump and/or motion of at least one first or second seal controls liquid flow out of the actuation pump.

8. A dispenser as claimed in claim 7 wherein the actuation pump is configured such that motion of the first seal controls the liquid flow into the actuation pump, and the second seal controls liquid flow out of the actuation pump.

9. A dispenser as claimed in claim 1 wherein the dosing pump is in part defined between a first seal and a second seal, and wherein at least one first or second seal controls liquid flow into, and out of, the dosing pump.

10. A dispenser as claimed in claim 9 wherein the first seal controls liquid flow into and out of the dosing pump, and the second seal controls liquid flow out of the dosing pump.

11. A dispenser as claimed in claim 10 wherein the second seal comprises the tip seal.

12. A dispenser as claimed in claim 1 wherein the actuation pump and dosing pump share a common seal.

13. A dispenser as claimed in claim 12 wherein the common seal controls a volume of a dispensed droplet in conjunction with the housing.

14. A dispenser as claimed in claim 1 further comprising a gas filled plenum in flow communication with the dosing pump.

15. A dispenser as claimed in claim 1, further comprising an actuator comprising a movable coupling and a first vacuum chamber, wherein the movable coupling is provided with a driver, operable to move the coupling in a first direction to expand the first vacuum chamber, wherein movement of the driver in the first direction expands the first vacuum chamber from a contracted state, and wherein release of the driver allows the first vacuum chamber to return to the contracted state, moving the coupling in a second direction, independent of the driver.

16. A dispenser as claimed in claim 15 wherein the first vacuum chamber is defined by the housing and by the coupling.

17. A dispenser as claimed in claim 15 wherein the driver is selectively coupled to the coupling by a second vacuum chamber.

18. A dispenser as claimed in claim 17 wherein the second vacuum chamber is provided with a vacuum release which operates to vent the second vacuum chamber when the coupling reaches the vacuum release upon movement in the first direction, thereby decoupling the driver from the first vacuum chamber.

19. A method of delivering a droplet of medication comprising the steps of;
  filling a dosing pump with a medication, and then filling an actuation pump with the medication,
  then contracting the actuation pump and contracting the dosing pump, such that a tip seal is lifted away from an outlet orifice by the contraction of the actuation pump,
  and then venting the actuation pump to close the tip seal against the outlet orifice to seal it,
  wherein contraction of the dosing pump delivers a dose of the medication to an outlet nozzle at a first speed as the tip seal is lifted away from the outlet orifice, and at a second, higher speed as the tip seal is closed against the outlet nozzle, wherein the actuation pump operates at a hydraulic pressure which is higher than the dosing pump.

20. A method as claimed in claim 19 comprising the further steps of expanding a first vacuum chamber from a contracted state as the dosing pump is filled, and as the actuation pump is filled,
  and then allowing the vacuum chamber to contract to the contracted state, wherein the vacuum chamber is coupled to the dosing pump and the actuation pump such that the contraction of the vacuum chamber drives the contraction of the actuation pump and contraction of the dosing pump.

* * * * *